United States Patent
Ueyama et al.

(10) Patent No.: US 10,568,824 B2
(45) Date of Patent: *Feb. 25, 2020

(54) SKIN COSMETIC

(71) Applicant: Kao Corporation, Tokyo (JP)

(72) Inventors: Chihiro Ueyama, Ichikawa (JP); Tomokazu Yoshida, Suginami-ku (JP); Takashi Fukui, Kawasaki (JP); Masanori Orita, Shiroi (JP)

(73) Assignee: Kao Corporation, Tokyo (JP)

(*) Notice: Subject to any disclaimer, the term of this patent is extended or adjusted under 35 U.S.C. 154(b) by 0 days.

This patent is subject to a terminal disclaimer.

(21) Appl. No.: 15/028,809

(22) PCT Filed: Apr. 10, 2015

(86) PCT No.: PCT/JP2015/061220
§ 371 (c)(1),
(2) Date: Apr. 12, 2016

(87) PCT Pub. No.: WO2015/182261
PCT Pub. Date: Dec. 3, 2015

(65) Prior Publication Data
US 2016/0235641 A1  Aug. 18, 2016

(30) Foreign Application Priority Data
May 30, 2014  (JP) ................. 2014-113232

(51) Int. Cl.
A61K 8/43    (2006.01)
A61K 8/29    (2006.01)
A61K 8/19    (2006.01)
A61K 8/34    (2006.01)
A61K 8/36    (2006.01)
A61Q 19/00   (2006.01)

(52) U.S. Cl.
CPC .......... A61K 8/43 (2013.01); A61K 8/19 (2013.01); A61K 8/29 (2013.01); A61K 8/342 (2013.01); A61K 8/361 (2013.01); A61K 2800/10 (2013.01); A61Q 19/007 (2013.01)

(58) Field of Classification Search
None
See application file for complete search history.

(56) References Cited

U.S. PATENT DOCUMENTS

2003/0194445 A1* 10/2003 Kuhner ................. A01N 37/46
                                                    424/622
2015/0110840 A1   4/2015 Yoshida et al.

FOREIGN PATENT DOCUMENTS

| JP | 2006-36763 | 2/2006 |
| JP | 2006-56851 | 3/2006 |
| JP | 2006-290751 | 10/2006 |
| JP | 2006-312622 | 11/2006 |
| JP | 2007-9199 | 1/2007 |
| JP | 2010-150164 | 7/2010 |
| JP | 2016-55907 A | 4/2016 |
| JP | 2916-60516 A | 4/2016 |
| WO | 2015/056807 A1 | 4/2015 |

OTHER PUBLICATIONS

Sigma Aldrich "Tween 60", <http://www.sigmaaldrich.com/catalog/product/sigma/p1629?lang=en&region=US>, accessed Aug. 5, 2017.*
International Search Report dated Jul. 14, 2015 in PCT/JP2015/061220 filed Apr. 10, 2015.
J. Soc. Cosmet. Chem. Jpn., vol. 46, No. 1, 2012, pp. 25-32 (with Partial English Translation).

* cited by examiner

Primary Examiner — Nicole P Babson
(74) Attorney, Agent, or Firm — Oblon, McClelland, Maier & Neustadt, L.L.P.

(57) ABSTRACT

The present invention provides a skin cosmetic containing the following components (A), (B), (C), (D), (E), and (F):
(A) 0.5 to 6 mass % of a linear saturated fatty acid having 12 to 22 of carbon atom,
(B) 0.010 to 5 mass % of an organic base,
(C) 0.010 to 1 mass % of an inorganic base,
(D) 0.5 to 6 mass % of a linear saturated alcohol having 12 to 22 of carbon atom,
(E) 0.05 to 9 mass % of a powder, and
(F) water, wherein
the component (D) comprises at least a linear saturated alcohol having 12 to 20 of carbon atom, and
the mass ratio of the component (E) to the total amount of the components (A) and (D) [(A)+(D)] is (E)/[(A)+(D)]=from 0.01 to 5.

12 Claims, No Drawings

SKIN COSMETIC

TECHNICAL FIELD

The present invention relates to a skin cosmetic.

BACKGROUND ART

Cosmetic compositions are supplemented with a powder from the viewpoint of producing an ultraviolet protective effect or the aesthetic appearance of the skin.

For example, Patent Literature 1 discloses that an external preparation for the skin in the form of an emulsion containing an optionally surface-treated metal oxide complex dispersed in an aqueous phase exerts color rendering properties or favorable improvement of appearance via makeup.

In response to a rise in health consciousness, particularly, dry skin consciousness, in recent years, there has been a demand for a cosmetic composition having a high moisturizing effect in addition to the aforementioned purposes.

As a skincare formula which exerts a high moisturizing effect, expectations have been placed on a cosmetic composition based on a layered $\alpha$-gel (e.g., Non Patent Literature 1). The $\alpha$-gel has a hydrated crystalline structure and has a lamellar structure. Most of horny layer intercellular lipids present in the stratum corneum, which is the outermost layer of the skin, assume this lamellar structure, and this structure suppresses invasion of a substance from the outside to the skin and water loss from the inside while the structure itself functions to retain moisture, thereby keeping the softness and smooth appearance of the skin.

For example, Patent Literature 2 discloses that a cosmetic composition containing a particular quaternary ammonium-type cationic surfactant, an amphipathic lipid, a dihydric or trihydric alcohol, a powder, and water has an $\alpha$-gel structure and offers a non-sticky feel.

Patent Literature 3 discloses that a cosmetic comprising a lamellar liquid-crystal structure and/or a liposome as a backbone in which at least one of a pigment and a powder is incorporated into the lamellar liquid-crystal structure and a water-soluble active ingredient is incorporated into an aqueous phase portion of the liposome is excellent in skin barrier effect.

(Patent Literature 1) JP-A-2010-150164
(Patent Literature 2) JP-A-2006-36763
(Patent Literature 3) JP-A-2006-56851
(Non Patent Literature 1) J. Soc. Cosmet. Chem. Jpn. 46 (1) 25-32 (2012)

SUMMARY OF INVENTION

The present invention relates to a skin cosmetic comprising the following components (A), (B), (C), (D), (E), and (F)
(A) 0.5 to 6 mass % of a linear saturated fatty acid having 12 to 22 of carbon atom,
(B) 0.010 to 5 mass % of an organic base,
(C) 0.010 to 1 mass % of an inorganic base,
(D) 0.5 to 6 mass % of a linear saturated alcohol having 12 to 22 of carbon atom,
(E) 0.05 to 9 mass % of a powder, and
(F) water, wherein
the component (D) comprises at least a linear saturated alcohol having 12 to 20 of carbon atom, and
the mass ratio of the component (E) to the total amount of the components (A) and (D) [(A)+(D)] is (E)/[(A)+(D)]=from 0.01 to 5.

DETAILED DESCRIPTION OF INVENTION

The cosmetic composition described in Patent Literature 2 results in the breakage of the $\alpha$-gel structure during application. In the cosmetic described in Patent Literature 3, the sustention of a moisturizing effect and the sustention of the effects of the powder are not clear, though the powder is incorporated into the lamellar liquid-crystal structure.

The present invention relates to a skin cosmetic which forms a homogenous soft film having a lamellar $\alpha$-gel structure on the surface of the skin when applied to the skin, produces high moisture-confining properties against water loss from the skin, i.e., high moisturizing properties, in a low humid environment, offers no stickiness upon application, effectively exerts the effects of the powder because the powder is uniformly dispersed, also renders the coating film less likely to come off against friction after application, and sustains the effects of the powder for a long time.

The present invention relates to a cosmetic having the following effects: the cosmetic offers no stickiness upon application, forms a film (coating film) having a lamellar $\alpha$-gel structure on the surface of the skin after being applied to the skin, and produces high moisture-confining properties against water loss from the skin, i.e., high moisturizing properties, in a low humid environment. Furthermore, the cosmetic effectively exerts the effects of the powder because the powder is uniformly dispersed in the coating film, also renders the coating film less likely to come off against friction after application, and exerts the sustained effects of the powder for a long time.

The present inventors have found that a skin cosmetic which offers no stickiness upon application, forms a film (coating film) having a lamellar $\alpha$-gel structure on the surface of the skin after being applied to the skin, has high moisture-confining properties against water loss from the skin, i.e., high moisturizing properties, in a low humid environment, effectively exerts the effects of the powder because the powder is uniformly dispersed in the coating film, also renders the film less likely to come off against friction after application, and exerts the sustained effects of the powder for a long time is obtained by combining a particular saturated fatty acid, a saturated alcohol, an organic base, an inorganic base, a powder, and water at a particular ratio.

The skin cosmetic of the present invention offers no stickiness upon application, forms a film (coating film) having a lamellar $\alpha$-gel structure on the surface of the skin after being applied to the skin, has high moisture-confining properties against water loss from the skin, i.e., high moisturizing properties, in a low humid environment, effectively exerts the effects of the powder because the powder is uniformly dispersed in the coating film, also renders the film less likely to come off against friction after application, and exerts the sustained effects of the powder for a long time.

(A) Linear Saturated Fatty Acid Having 12 to 22 of Carbon Atom:

The component (A) used in the present invention is a linear saturated fatty acid having 12 to 22 of carbon atom, and examples thereof include lauric acid, myristic acid, palmitic acid, stearic acid, and behenic acid. Among them, a linear saturated fatty acid having 14 to 22 of carbon atom is preferred, a linear saturated fatty acid having 16 to 22 of carbon atom is more preferred, and palmitic acid or stearic acid is further preferred from the viewpoint of forming a film having a stable lamellar $\alpha$-gel structure in the cosmetic. Stearic acid is still further preferred from the viewpoint of the stability of the lamellar $\alpha$-gel structure.

At least one or two or more selected from the group consisting of these linear saturated fatty acids having 12 to 22 of carbon atom can be used as the component (A) and can form a lamellar α-gel structure in the cosmetic by neutralization with the components (B) and (C) mentioned later. Thus, the component (A) is present as a fatty acid or a salt thereof in the cosmetic. In the present invention, the content of the component (A) is an amount in terms of the fatty acid.

The content of the component (A) in the whole composition is 0.5 mass % or more, preferably 1.0 mass % or more, more preferably 1.5 mass % or more, and is 6 mass % or less, preferably 4 mass % or less, more preferably 3.8 mass %; or less, from the viewpoint of forming a stable lamellar α-gel structure in the cosmetic. Also, the content of the component (A) in the whole composition is from 0.5 to 6 mass %, preferably from 1.0 to 4 mass %, more preferably from 1.5 to 3.8 mass %.

(B) Organic Base:

The component (B) used in the present invention is an organic base, and examples thereof include alkylamines having an alkyl group having 1 to 6 of carbon atom, alkanolamines having an alkyl group having 1 to 6 of carbon atom, and basic amino acids. The component (B) functions as a neutralizing agent for the component (A).

Specifically, examples of the alkylamines include methylamine, ethylamine, propylamine, butylamine, hexylamine, dimethylamine, and diethylamine.

Examples of the alkanolamines include monoethanolamine, diethanolamine, triethanolamine, 2-amino-2-hydroxymethyl-1,3-propanediol, N-methyl-diethanolamine, N,N-dimethyl monoethanolamine, and aminomethyl propanol. At least any one selected from the group consisting of triethanolamine, 2-amino-2-hydroxymethyl-1,3-propanediol, and aminomethyl propanol is preferred, and aminomethyl propanol is more preferred.

Examples of the basic amino acids include lysine, histidine, and arginine. Arginine is preferred. The arginine is preferably L-arginine.

Among them, an alkanolamine having an alkyl group having 1 to 6 of carbon atom or a basic amino acid having 1 to 6 of carbon atom is preferred, an alkanolamine having an alkyl group having 3 to 6 of carbon atom or a basic amino acid having 3 to 6 of carbon atom is more preferred, a basic amino acid is further preferred, aminomethyl propanol or arginine is still further preferred, and arginine is still further preferred, from the viewpoint of neutralizing the component (A) and forming a stable lamellar structure in the cosmetic and from the viewpoint of enhancing moisturizing properties. The arginine is preferably L-arginine.

At least one or two or more selected from the group consisting of these organic bases can be used as the component (B). The molar ratio of the component (B) to the component (A) is preferably 10 mol % or more, more preferably 30 mol % or more, and is preferably 80 mol % or less, more preferably 60 mol % or less, from the viewpoint of enhancing the stability of the α-gel structure in the coating film of the skin cosmetic and from the viewpoint of enhancing moisturizing properties.

The content of the component (B) in the whole composition is 0.010 mass % or more, preferably 0.02 mass % or more, more preferably 0.05 mass % or more, further preferably 0.1 mass % or more, and is 5 mass % or less, preferably 2 mass % or less, more preferably 0.8 mass % or less, further preferably 0.4 mass % or less, from the viewpoint of enhancing the stability of the α-gel structure in the coating film of the skin cosmetic and enhancing moisturizing properties. The content of the component (B) in the whole composition is from 0.010 to 5 mass %, preferably from 0.02 to 2 mass %, more preferably from 0.05 mass % to 0.8 mass %, further preferably from 0.1 to 0.4 mass %.

The component (B) may form salts with the component (A) and other acids in the cosmetic. In the present invention, the content of the component (B) is an amount in terms of the organic base.

(C) Inorganic Base:

The component (C) used in the present invention is an inorganic base, and examples thereof include alkali metal hydroxides such as sodium hydroxide and potassium hydroxide. The component (C) functions as a neutralizing agent for the component (A).

Among them, sodium hydroxide or potassium hydroxide is preferred, and sodium hydroxide is more preferred, from the viewpoint of neutralizing the component (A) and forming a stable lamellar α-gel structure in the cosmetic.

At least one or two or more selected from the group consisting of these inorganic bases can be used as the component (C). The molar ratio of the component (C) to the component (A) is preferably 10 mol % or more, more preferably 30 mol % or more, and is preferably 80 mol % or less, more preferably 60 mol % or less, from the viewpoint of enhancing the stability of the lamellar α-gel structure in the skin cosmetic and enhancing moisturizing properties.

The content of the component (C) in the whole composition is 0.010 mass % or more, preferably 0.04 mass % or more, more preferably 0.08 mass % or more, and is 1 mass % or less, preferably 0.3 mass % or less, more preferably 0.25 mass % or less, from the viewpoint of enhancing the stability of the lamellar α-gel structure in the skin cosmetic and enhancing moisturizing properties. The content of the component (C) in the whole composition is from 0.010 to 1 mass %, preferably from 0.04 to 0.3 mass %, more preferably from 0.08 to 0.25 mass %.

The component (C) may form salts with the component (A) and other acids in the cosmetic. In the present invention, the content of the component (C) is an amount in terms of the inorganic base.

In the present invention, the molar ratio of the component (B) to the total amount of the components (B) and (C) [(B)+(C)], (B)/[(B)+(C)], is preferably 5 or more, more preferably 8 or more, further preferably 10 or more, and is preferably 75 or less, more preferably 70 or less, further preferably 65 or less, from the viewpoint of forming a film having a lamellar α-gel structure excellent in moisture-confining properties. The molar ratio of the component (B) to the total amount of the components (B) and (C) [(B)+(C)], (B)/[(B)+(C)], is preferably from 5 to 75, more preferably from 8 to 70, further preferably from 10 to 65.

The molar ratio of the total amount of the components (B) and (C) [(B)+(C)] to the component (A), [(B)+(C)]/(A), represents the degree of neutralization and is preferably 10 or more, more preferably 20 or more, further preferably 30 or more, and is preferably 110 or less, more preferably 100 or less, further preferably 90 or less, from the viewpoint of forming a film having a lamellar α-gel structure excellent in moisture-confining properties. The molar ratio of the total amount of the components (B) and (C) [(B)+(C)] to the component (A), [(B)+(C)]/(A), is preferably [(B)+(C)]/(A)=from 10 to 110, more preferably from 20 to 100, further preferably from 30 to 90.

The combination of the component (B) and the component (C) is preferably aminomethyl propanol or arginine as the component (B) and sodium hydroxide or potassium hydroxide as the component (C), more preferably arginine as the component (B) and sodium hydroxide as the component (C), from a similar viewpoint.

(D) Linear Saturated Alcohol Having 12 to 22 of Carbon Atom:

The component (D) used in the present invention is a linear saturated alcohol having 12 to 22 of carbon atom, and examples thereof include lauryl alcohol, myristyl alcohol, cetyl alcohol, stearyl alcohol, and behenyl alcohol. Among them, a linear saturated alcohol having 14 to 22 of carbon atom is preferred, and a linear saturated alcohol having 16 to 22 of carbon atom is more preferred. Cetyl alcohol or stearyl alcohol is further preferred, and still further preferably, the component (D) comprises cetyl alcohol and stearyl alcohol, from the viewpoint of stabilizing the lamellar α-gel structure formed by the component (A) in the cosmetic. When the component (D) contains ethyl alcohol and stearyl alcohol, these alcohols may be contained each independently or as a mixture, or cetostearyl alcohol, which is a mixture thereof, may be contained.

The component (D) used in the present invention is a linear saturated alcohol having 12 to 22 of carbon atom and contains at least a linear saturated alcohol having 12 to 20 of carbon atom. The phrase "containing at least a linear saturated alcohol having 12 to 20 of carbon atom" conceptually encompasses the case where the component (D) comprises, for example, a linear saturated alcohol having 14 of carbon atom and a linear saturated alcohol having 16 of carbon atom. Examples of the linear saturated alcohol having 12 to 22 of carbon atom include lauryl alcohol, myristyl alcohol, cetyl alcohol, stearyl alcohol, and behenyl alcohol. Among them, a linear saturated alcohol having 14 to 22 of carbon atom is preferred, a linear saturated alcohol having 16 to 22 of carbon atom is more preferred, and a linear saturated alcohol having 16 to 20 of carbon atom is even more preferred. Cetyl alcohol or stearyl alcohol is further preferred, and still further preferably, the component (D) comprises cetyl alcohol and stearyl alcohol, from the viewpoint of stabilizing the lamellar α-gel structure formed by the component (A) in the cosmetic. When the component (D) comprises cetyl alcohol and stearyl alcohol, these alcohols may be contained each independently or as a mixture, or cetostearyl alcohol, which is a mixture thereof, may be contained.

The component (D) comprises at least the aforementioned linear saturated alcohol having 12 to 20 of carbon atom, and one or two or more selected from the group consisting f these linear saturated alcohols having 12 to 22 of carbon atom can be used. The content thereof in the whole composition is 0.5 mass % or more, preferably 1 mass % or more, more preferably 1.3 mass % or more, and is 6 mass % or less, preferably 5.5 mass % or less, more preferably 5.2 mass % or less, from the viewpoint of stabilizing the lamellar α-gel structure in the cosmetic. Also, the content of the component (D) in the whole composition is from 0.5 to 6 mass %, preferably from 1 to 5.5 mass %, more preferably from 1.3 to 5.2 mass %.

In the present invention, the total amount of the components (A) and (D), (A)+(D), in the whole composition is preferably 1 mass % or more, more preferably 2 mass % or more, further preferably 3 mass % or more, from the viewpoint of forming a uniform α-gel coating film on the skin, and is preferably 12 mass % or less, more preferably 9.5 mass % or less, further preferably 8 mass % or less, from the viewpoint of suppressing stickiness upon application of the cosmetic composition. The total amount of the components (A) and (D), (A)+(D), in the whole composition is preferably from 1 to 12 mass %, more preferably from 2 to 9.5 mass %, further preferably from 3 to 8 mass %.

The mass ratio of the component (A) to the total amount of the components (A) and (D) [(A)+(D)], (A)/[(A)+(D)], is preferably 0.2 or more, more preferably 0.25 or more, further preferably 0.27 or more, still further preferably 0.30 or more, and is preferably 0.7 or less, more preferably 0.65 or less, further preferably 0.60 or less, still further preferably 0.55 or less, from the viewpoint of forming a lamellar α-gel structure in the cosmetic composition while enhancing moisturizing properties. The mass ratio of the component (A) to the total amount of the components (A) and (D) [(A)+(D)], (A)/[(A)+(D)], is preferably from 0.2 to 0.7, more preferably from 0.25 to 0.65, further preferably from 0.27 to 0.60, still further preferably from 0.3 to 0.55.

(E) Powder:

The component (E) used in the present invention is a powder and is used according to the purpose, for example, from the viewpoint of producing an ultraviolet protective effect or the aesthetic appearance of the skin. The powder as the component (E) is not limited as long as the powder can be usually used in cosmetics. Any of inorganic powders, organic powders, powders composed of fiber, starches, and the like can be preferably used, and its shape can be any of a spherical shape, a plate shape, and the like. The internal structure of the powder is not particularly limited, and any of porous, hollow, and nonporous structures, and the like can be used. These powders are not dissolved in water, alcohols, oil agents, or the like.

Examples of the inorganic powders include titanium oxide, zinc oxide, magnesium oxide, zirconium oxide, calcium carbonate, magnesium carbonate, magnesium silicate, barium sulfate, silica (silicic anhydride), mica, talc, kaolin, sericite, colcothar, yellow oxide of iron, black oxide of iron, carbon black, manganese violet, glass beads, zeolite, pearl pigments (colcothar-coated mica, titanium oxide-coated mica, etc.), and complexes thereof.

Examples of the organic powders include thermoplastic resins such as acrylic resins, styrene resins, polyolefins, silicone resins, fluorine resins, polyester resins, and polyamides, epoxy resins, phenol resins, and urethane resins.

Examples of the powders composed of fiber include silk, wool, and cellulose. Examples of the starches include rice, corn, and potato starches. Also, complexes of these powders can be used.

Among these powders, titanium oxide, talc, iron oxide, silica, or (lauryl methacrylate/sodium methacrylate) crosspolymer is preferred, and titanium oxide is more preferred, from the viewpoint of producing aesthetic appearance in such a way to brighten skin color or conceal blemishes. These inorganic powders can also be used as ultraviolet protective agents.

Among these powders, titanium oxide or zinc oxide is preferred, and titanium oxide is more preferred, from the viewpoint of producing an ultraviolet protective effect. It is further preferred to use the powder together with an ultraviolet absorber mentioned later, from the viewpoint of producing an ultraviolet protective effect.

The powder as the component (E) has a volume-average particle size of preferably 0.005 μm or larger, more preferably 0.01 μm or larger, further preferably 0.05 μm, still further preferably 0.07 μm or larger, particularly preferably 0.1 μm or larger, and of preferably 10 μm or smaller, more preferably 5 μm or smaller, further preferably 3 μm or smaller, still further preferably 1 μm or smaller, particularly preferably 0.5 μm or smaller, from the viewpoint of suppressing stickiness upon application of the skin cosmetic and uniformly dispersing the powder in the coating film. The volume-average particle size of the powder is preferably from 0.005 to 10 μm, more preferably from 0.01 to 5 μm, further preferably from 0.05 to 3 μm, still further preferably from 0.07 to 1 μm, and still further preferably from 0.1 to 0.5 μm.

In the present invention, the volume-average particle size means a median size which is calculated from a volume-based particle size distribution measured by a laser diffraction/scattering method using a laser diffraction/scattering-type particle size distribution analyzer (e.g., manufactured by Horiba, Ltd., LA-920).

The powder as the component (E) has a volume-average particle size of preferably 0.005 μm or larger, more preferably 0.007 μm or larger, further preferably 0.01 μm or larger, and of preferably 0.2 μm or smaller, more preferably 0.1 μm or smaller, further preferably 0.05 μm or smaller, from the aforementioned viewpoint as well as from the viewpoint of producing an ultraviolet protective effect. The volume-average particle size of the powder is preferably from 0.005 to 0.2 μm, more preferably from 0.007 to 0.1 μm, further preferably from 0.01 to 0.05.

This volume-average particle size is obtained by measuring the maximum minor axes of the particle sizes of 300 particles in an image under ×100,000 conditions in a transmission electron microscope (TEM) and calculating an average thereof. In this context, the maximum minor axis means a minor axis having the largest size among minor axes orthogonal to the major axis.

A powder whose surface has undergone hydrophilizing treatment or hydrophobizing treatment can be used as the component (E). Examples of the hydrophilizing treatment include treatment methods such as silica treatment, alumina treatment, silica-alumina treatment, amino acid treatment, and polyacrylic acid treatment. Examples of the hydrophobizing treatment include: a fat treatment method which involves rendering the powder lipophilic by adsorbing a fat onto the powder surface or causing esterification or etherification by use of a functional group such as a hydroxy group; a metallic soap treatment method using fatty acid zinc salt, magnesium salt, or aluminum salt; a silicone treatment method using a silicone compound such as dimethylsiloxane, trimethoxycaprylylsilane, triethoxycaprylylsilane, or methyl hydrogen siloxane; and a method for treatment with a fluorine compound having a perfluoroalkyl group. Since the skin cosmetic of the present invention contains a hydrophilic portion and a lipophilic portion, a powder which has undergone hydrophilizing treatment and a powder which has undergone hydrophobizing treatment may both be used.

Metallic soap treatment using fatty acid zinc salt, fatty acid magnesium salt, or fatty acid aluminum salt, silicone treatment using a silicone compound such as dimethylsiloxane, trimethoxycaprylylsilane, triethoxycaprylylsilane, or methyl hydrogen siloxane, or amino acid treatment using sodium stearoyl glutamate is preferred from the viewpoint of producing an ultraviolet protective effect.

At least one or two or more selected from the group consisting of these powders can be used as the component (E). The content thereof in the whole composition is 0.05 mass % or more, preferably 0.08 mass % or more, more preferably 0.1 mass % or more, further preferably 0.4 mass % or more, and is 9 mass % or less, preferably 5 mass % or less, more preferably 4 mass % or less, further preferably 2 mass % or less, from the viewpoint of uniformly dispersing the powder in the coating film and efficiently brightening skin color. The content of the component (E) in the whole composition is from 0.05 to 9 mass %, preferably from 0.08 to 5 mass %, more preferably from 0.1 to 4 mass %, further preferably from 0.4 to 2 mass % or less.

Furthermore, the content of the component (E) in the whole composition is 0.05 mass % or more, preferably 1 mass % or more, more preferably 1.5 mass % or more, further preferably 2.5 mass % more, still further preferably 3 mass % or more, and is 9 mass % or less, preferably 7 mass % or less, more preferably 6 mass % or less, further preferably 5 mass % or less, still further preferably 4.5 mass % or less, from the aforementioned viewpoint as well as from the viewpoint of producing an ultraviolet protective effect. The content of the component (E) in the whole composition is from 0.05 to 9 mass %, preferably from 1 to 7 mass %, more preferably from 1.5 to 6 mass %, further preferably from 2.5 to 5 mass % or less, still further preferably from 3 to 4.5 mass % or less.

In the present invention, the mass ratio of the component (E) to the total amount of the components (A) and (D) [(A)+(D)], (E)/[(A)+(D)], is 0.01 or more, preferably 0.05 or more, more preferably 0.07 or more, further preferably 0.1 or more, and is 5 or less, preferably 4 or less, more preferably 3 or less, further preferably 1 or less, from the viewpoint of effectively exerting the effects of the powder when the cosmetic composition is applied to the skin, and from the viewpoint of rendering the coating film less likely to come off against friction after application and sustaining the effects of the powder for a long time. The mass ratio of the component (E) to the total amount of the components (A) and (D) [(A)+(D)], (E)/[(A)+(D)], is from 0.01 to 5, preferably from 0.05 to 4, more preferably from 0.07 to 3, further preferably 0.1 to 1.

(F) Water:

The component (F) used in the present invention water and serves as a solvent for the cosmetic of the present invention. The component (F) becomes a balance of the components. The components (A) to (F) can be combined to form a stable lamellar α-gel structure in the cosmetic.

The content of the component (F) in the whole composition is preferably 50 mass % or more, more preferably 60 mass % or more, and is preferably 96 mass % or less, more preferably 95 mass % or less, from the viewpoint of offering no stickiness and forming a stable lamellar α-gel structure in the cosmetic. The content of the component (F) in the whole composition is preferably from 50 to 98 mass %, more preferably from 60 to 96 mass %.

Furthermore, the content of the component (F) in the whole composition is preferably 50 mass % or more, more preferably 60 mass % or more, and is preferably 98 mass % or less, more preferably 96 mass % or less, from the viewpoint of offering no stickiness and forming a stable lamellar α-gel structure in the cosmetic. The content of the component (F) in the whole composition is preferably from 50 to 98 mass %, more preferably from 60 to 96 mass %.

The skin cosmetic of the present invention comprising the components (A) to (F) forms an α-gel structure. This cosmetic is applied to the skin to form a cosmetic coating film on the surface of the skin as a result of water evaporation. This coating film also forms an α-gel and has a lamellar structure. The lamellar structure is a structure similar to the intercellular lipids of the skin and can retain moisture between the lamellar layers. In addition, this film is excellent in moisture-confining properties and therefore suppresses water loss from the skin. Hence, the film can impart moisture to the skin and can produce high moisturizing properties. Furthermore, the skin cosmetic of the present invention offers no stickiness upon application and effectively exerts the effects of the powder because the powder is uniformly dispersed in the coating film. The skin cosmetic of the present invention further renders the coating film less likely to come off against friction after application and sustains the effects of the powder for a long time. This is probably because the coating film formed from the skin cosmetic of the present invention has higher softness than that of conventional cosmetics.

(G) Nonionic Surfactant:

In the present invention, the skin cosmetic can further contain a nonionic surfactant from the viewpoint of facilitating forming the lamellar α-gel structure as described above and improving the stability of the α-gel structure in the coating film and from the viewpoint of effectively exerting the effects of the powder.

The nonionic surfactant can also suppress fine foams which are generated due to the friction between the skin and fingers when the skin cosmetic of the present invention is applied to the skin by fingers. As a result, the cosmetic can be well spread over the skin when applied thereto.

Examples of the nonionic surfactant include: ethylene glycol fatty acid esters such as ethylene glycol monostearic acid ester; polyethylene glycol fatty acid esters such as polyethylene glycol (2) monostearic acid ester; polyalkylene glycol alkyl ethers such as polyethylene glycol (5) decyl pentadecyl ether; polyethylene glycol hydrogenated castor oils such as polyethylene glycol (5) hydrogenated castor oil monoisolaurate; propylene glycol fatty acid esters; monoglycerin monofatty acid esters such as glycerin monoisostearic acid ester; monoglycerin difatty acid esters such as glycerin distearic acid ester and glycerin dilauric acid ester; glycerin alkyl ethers such as glycerin monoisostearyl ether; sorbitan fatty acid esters such as sorbitan monostearic acid ester; fatty acid alkanolamides; and fatty acid dialkanolamides such as lauric acid diethanolamide.

Among these nonionic surfactants, a polyalkylene glycol alkyl ether having an alkyl group having 12 to 22 of carbon atom is preferred, and a polyalkylene glycol ether having an alkyl group having 12 to 18 of carbon atom is more preferred, from the viewpoint of suppressing fine foams upon application.

At least one or two or more selected from the group consisting of these nonionic surfactants can be used as the nonionic surfactant as the component (G). At least one nonionic surfactant has an HLB of preferably from 8 to 19, more preferably from 10 to 16, from the viewpoint of effectively exerting the effects of the powder. The HLB value is an index for hydrophile lipophile balance. In the present invention, a value calculated according to the following expression of Oda and Teramura, et al., is used.

$$HLB = \frac{\sum \text{Inorganic value}}{\sum \text{Organic value}} \times 10$$

Ceteareth-20, which is a mixture of stearyl alcohol and polyethylene glycol ether, is more preferably contained as the nonionic surfactant as the component (G).

The content of the nonionic surfactant as the component (G) in the whole composition is preferably 0.05 mass % or more, more preferably 0.1 mass % or more, further preferably 0.2 mass % or more, and is preferably 2 mass % or less, more preferably 1.5 mass % or less, further preferably 1 mass % or less, from the viewpoint of improving moisturizing properties, from the viewpoint of suppressing sliminess, from the viewpoint of improving stability, and from the viewpoint of suppressing foaming of the cosmetic composition upon application. The content of the component (G) in the whole composition is preferably from 0.05 to 2 mass %, more preferably from 0.1 to 1.5 mass %, further preferably from 0.2 to 1 mass %.

The mass ratio of the total amount of the components (A) and (D) [(A)+(D)] to the component (G), [(A)+(D)]/G, is preferably 2 or more, more preferably 3 or more, further preferably 4 or more, and is preferably 30 or less, more preferably 20 or less, further preferably 10 or less, from the viewpoint of improving moisturizing properties, from the viewpoint of suppressing sliminess, from the viewpoint of improving stability, and from the viewpoint of suppressing foaming of the cosmetic composition. The mass ratio of the total amount of the components (A) and (D) [(A)+(D)] to the component (G), [(A)+(D)]/G, is preferably from 2 to 30, more preferably from 3 to 20, further preferably from 4 to 10.

The skin cosmetic of the present invention can further contain, as a component (H), at least one compound selected from the group consisting of vitamins B3 and vitamins C. The skin cosmetic of the present invention rapidly forms a film having a lamellar α-gel structure when applied to the skin. Thus, stickiness derived from the α-gel or such vitamins is hardly perceivable upon application. Since a soft α-gel film carrying the active ingredient is uniformly formed on the skin, the active ingredient acts both on the cristae cutis and on the sulci cutis and the skin cosmetic can keep the skin smooth even after a lapse of time from the application. The active ingredient used in combination with the powder can further produce the effect of preventing the lateral diffusion of the active ingredient on the skin. This is probably because the combination with the component (E) produces the softness of the coating film as well as its rigidity.

The component (H) is used according to the purpose, for example, from the viewpoint of producing an antioxidative effect or a whitening effect.

The component (H) is not limited as long as the component (H) can be usually used in cosmetics. Examples of the vitamins B3 include nicotinic acid and niacinamide. Examples of the vitamins C include L-ascorbic acid, magnesium ascorbyl phosphate, sodium ascorbyl phosphate, ascorbic acid 2-glucoside, and ascorbic acid palmitate.

Among these active ingredients, a water-soluble agent is preferred because the α-gel is a hydrated solid. Water-soluble vitamins 33 and vitamins C are preferred.

Vitamins B3 are preferred, water-soluble vitamins B3 are more preferred, and niacinamide is further preferred, from the viewpoint of improving the stability of the formula and a smooth skin feel.

The content of the component (H) in the whole composition is preferably 0.01 mass % or more, more preferably 0.05 mass % or more, further preferably 0.1 mass % or more, and is preferably 5 mass % or less, more preferably 4 mass % or less, further preferably 3 mass % less, from the viewpoint of the stability of the formula, the absence of stickiness, and a smooth skin feel. Also, the content of the component (H) in the whole composition is preferably from 0.01 to 5 mass %, more preferably from 0.05 to 4 mass %, further preferably from 0.1 to 3 mass %.

The mass ratio between the components (H) and (E), (H)/(E), is preferably 0.01 or more, more preferably 0.03 or more, further preferably 0.05 or more, and is preferably 5 or less, more preferably 3 or less, further preferably 2 or less, from the viewpoint of adsorbing the active ingredient by the powder and preventing the lateral diffusion of the active ingredient on the skin. The mass ratio between the components (H) and (E), (H)/(E), is preferably from 0.01 to 5, more preferably, from 0.03 to 3, further preferably from 0.05 to 2.

The skin cosmetic of the present invention can further contain an ultraviolet absorber as a component
(I) and can produce a higher ultraviolet protective effect.

The ultraviolet absorber is preferably oil-soluble, and examples thereof include benzoic acid ultraviolet absorbers, anthranilic acid ultraviolet absorbers, salicylic acid ultraviolet absorbers, cinnamic acid ultraviolet absorbers, benzophenone ultraviolet absorbers, and triazine ultraviolet absorbers.

The skin cosmetic of the present invention contains, as the ultraviolet absorber, preferably at least one selected from the group consisting of a benzoic acid ultraviolet absorber, a salicylic acid ultraviolet absorber, a cinnamic acid ultraviolet absorber, a benzophenone ultraviolet absorber, and a triazine ultraviolet absorber, more preferably at least one or more selected from the group consisting of a salicylic acid ultraviolet absorber, a cinnamic acid ultraviolet absorber, and a benzophenone ultraviolet absorber, further preferably at least two or more selected from the group consisting of a salicylic acid ultraviolet absorber, a cinnamic acid ultraviolet absorber, and a benzophenone ultraviolet absorber, from the viewpoint of enhancing an ultraviolet protective effect while suppressing stickiness.

Examples of the benzoic acid ultraviolet absorber include p-aminobenzoic acid (hereinafter, abbreviated to PABA), glyceryl PABA, ethyl dihydroxypropyl PABA, N-ethoxylated PABA ethyl ester, N-dimethyl PABA ethyl ester, N-dimethyl PABA butyl ester, N-dimethyl PABA amyl ester, octyl dimethyl PABA, and diethylamino hydroxybenzoyl hexyl benzoate. Among them, p-aminobenzoic acid or diethylamino hydroxybenzoyl hexyl benzoate is preferred, and diethylamino hydroxybenzoyl hexyl benzoate is more preferred, from the viewpoint of enhancing an ultraviolet absorbing effect while suppressing stickiness.

Examples of the anthranilic acid ultraviolet absorber include homomenthyl-N-acetyl anthranilate.

Examples of the salicylic acid ultraviolet absorber include amyl salicylate, menthyl salicylate, homomenthyl salicylate, octyl salicylate, phenyl salicylate, benzyl salicylate, and p-isopropanol phenyl salicylate. Among them, homomenthyl salicylate or octyl salicylate is more preferred from the viewpoint of enhancing an ultraviolet absorbing effect while suppressing stickiness.

Examples of the cinnamic acid ultraviolet absorber include octyl cinnamate, ethyl-4-isopropyl cinnamate, ethyl-2,4-diisopropyl cinnamate, methyl-2,4-diisopropyl cinnamate, propyl-p-methoxy cinnamate, isopropyl-p-methoxy cinnamate, isoamyl-p-methoxy cinnamate, 2-ethylhexyl-p-methoxy cinnamate, 2-ethoxyethyl-p-methoxy cinnamate, cyclohexyl-p-methoxy cinnamate, ethyl-α-cyano-β-phenyl cinnamate, 2-ethylhexyl-α-cyano-β-phenyl cinnamate, and glyceryl mono-2-ethylhexanoyl di-p-methoxy cinnamate. Among them, octyl cinnamate or 2-ethylhexyl-p-methoxy cinnamate is preferred, and 2-ethylhexyl-p-methoxy cinnamate is more preferred, from the viewpoint of enhancing an ultraviolet absorbing effect while suppressing stickiness.

Examples of the benzophenone ultraviolet absorber include 2,4-dihydroxybenzophenone, 2,2'-dihydroxy-4-methoxybenzophenone, 2,2'-dihydroxy-4,4'-dihydroxybenzophenone, 2-hydroxy-4-methoxybenzophenone, 2-hydroxy-4-methoxy-4'-methylbenzophenone, 2-hydroxy-4-methoxybenzophenone, 4-phenylbenzophenone, 2-ethylhexyl-4'-phenylbenzophenone-2-carboxylate, 2-hydroxy-4-n-octoxybenzophenone, and 4-hydroxy-3-carboxy-benzophenone. Among them, 2-hydroxy-4-methoxybenzophenone is more preferred from the viewpoint of, enhancing an ultraviolet absorbing effect while suppressing stickiness.

Examples of the triazine ultraviolet absorber include 2,4,6-tris[4-(2-ethylhexyloxycarbonyl)anilino]-1,3,5-triazine and 2,4-bis-[{4-(2-ethylhexyloxy)-2-hydroxy}-phenyl]-6-(4-methoxyphenyl)-1,3,5-triazine.

Other examples of the ultraviolet absorber include 3-(4'-methylbenzylidene)-dl-camphor, 3-benzylidene-dl-camphor, urocanic acid ethyl ester, 2-phenyl-5-methylbenzoxazole, 2,2'-hydroxy-5-methylphenyl benzotriazole, 2-(2'-hydroxy-5-t-octylphenyl)benzotriazole, dibenzalazine, dianisoylmethane, 4-tert-butylbenzoyl(4-methoxybenzoyl) methane, 5-(3,3-dimethyl-2-norbornylidene)-3-pentan-2-one, 2-ethylhexyl 2-cyano-3,3-diphenylacrylate, benzene bis-1,3-diketone derivatives described in JP-A-H2-212579, and benzoylpinacolone derivatives described in JP-A-H3-220153. Among them, 4-tert-butylbenzoyl(4-methoxybenzoyl)methane or 2-ethylhexyl 2-cyano-3,3-diphenylacrylate is more preferred from the viewpoint of enhancing an ultraviolet absorbing effect while suppressing stickiness.

One or two or more in combination of these ultraviolet absorbers can be used as the component (I). The combination and content thereof are determined according to, for example, the ultraviolet protective effect of the skin cosmetic of interest. The content of the ultraviolet absorber in the whole composition is preferably 0.1 mass % or more, more preferably 0.5 mass % or more, further preferably 3 mass % or more, still further preferably 5 mass % or more, from the viewpoint of exerting a higher ultraviolet protective effect of the skin cosmetic. The content of the ultraviolet absorber in the whole composition is preferably 30 mass % or less, more preferably 20 mass % or less, further preferably 18 mass % or less, still further preferably 15 mass % or less, from the viewpoint of further improving the usability of the skin cosmetic, i.e., from the viewpoint of suppressing stickiness and conferring a non-sticky feel.

In the present invention, the skin cosmetic can further contain an anionic surfactant, from the viewpoint of improving the stability of the lamellar structure, from the viewpoint of improving moisturizing properties, from the viewpoint of reducing an oily feel, from the viewpoint of improving the sustention of gloss, and from the viewpoint of suppressing foaming.

The anionic surfactant is selected from the group consisting of anionic surfactants except for the component (A), and examples thereof include: alkyl sulfuric acid esters having 12 to 22 of carbon atom or salts thereof, such as sodium lauryl sulfate and potassium lauryl sulfate; alkyl ether sulfuric acid esters having 12 to 22 of carbon atom or salts thereof, such as polyoxyethylene lauryl sulfate triethanolamine; N-acyl sarcosines having 12 to 22 of carbon atom or salts thereof, such as sodium lauroyl sarcosine; alkyl phosphates having 12 to 22 of carbon atom or salts thereof, such as sodium monostearyl phosphate; alkyl ether phosphates having 12 to 22 of carbon atom of polyoxyethylene or salts thereof, such as sodium polyoxyethylene oleyl ether phosphate and sodium polyoxyethylene stearyl ether phosphate; dialkyl sulfosuccinates having 12 to 24 of carbon atom or salts thereof, such as sodium di-2-ethylhexyl sulfosuccinate; N-alkyloyl methyltaurines having 12 to 22 of carbon atom or salts thereof, such as sodium N-stearoyl-N-methyltaurine; and N-acyl glutamates having 12 to 22 of carbon atom or salts thereof, such as sodium dilauroyl glutamate, monosodium N-lauroyl glutamate, sodium N-stearoyl-L-glutamate, arginine N-stearoyl-L-glutamate, sodium N-stearoyl glutamate, and sodium N-myristoyl-L-glutamate.

At least one or more selected from the group consisting of these anionic surfactants can be used as the anionic surfactant, and one of these anionic surfactants can be used alone, or two or more thereof can be used in combination.

The content of the anionic surfactant in the whole composition is preferably 1 mass % or less, more preferably 0.5 mass % or less, further preferably 0.3 mass % or less, still further preferably 0.1 mass % or less, from the viewpoint of improving the stability of the lamellar structure, from the viewpoint of improving moisturizing properties, from the viewpoint of reducing an oily feel, from the viewpoint of improving the sustention gloss, and from the viewpoint of suppressing foaming.

The skin cosmetic of the present invention can further contain a solid fat other than the components (A) and (D). The content thereof is preferably 5 mass % or less, more preferably 5 mass % or less, further preferably 1 mass % or less, still further preferably 0.5 mass % or less, from the viewpoint of stabilizing the lamellar structure.

The skin cosmetic of the present invention can further contain, appropriately, for example, a cationic surfactant, an amphoteric surfactant, a thickener, an oil component other than those described above, a microbicide, a moisturizer, a wetting agent, a colorant, an antiseptic, a feel-improving agent, a fragrance, an anti-inflammatory agent, a whitening agent, an antiperspirant, and an antioxidant as components for use in usual cosmetics, in addition to the component (A) to the component (I).

The skin cosmetic of the present invention can be produced, for example, by: mixing the components (B), (C), and (F) and homogeneously dissolving the mixture at from 60 to 100° C. to form an aqueous phase portion; mixing the components (A), (D), and (E) and homogeneously dissolving the mixture at from 60 to 100° C. to form an oil phase portion; and homogeneously mixing the aqueous phase portion with the oil phase portion and cooling the mixture to preferably from 20 to 45° C., more preferably from 25 to 40° C., further preferably from 30 to 35° C.

Alternatively, the skin cosmetic of the present invention can also be produced, for example, by: mixing the components (C) and (F) and homogeneously dissolving the mixture at from 60 to 100° C. to form an aqueous phase portion; mixing the components (A), (B), (D), and (E) and homogeneously dissolving the mixture at from 60 to 100° C. to form an oil phase portion; and homogeneously mixing the aqueous phase portion with the oil phase portion, followed by cooling.

The skin cosmetic of the present invention is obtained by the production method as described above and therefore eliminates the need of kneading the powder, for example, in a solvent, for dispersing the powder.

When the skin cosmetic of the present invention contains the component (G), this skin cosmetic can be produced, for example, by: mixing the components (B), (C), and (F) and homogeneously dissolving the mixture at from 60 to 100° C. to form an aqueous phase portion; mixing the components (A), (D), (E) (+(B)), and (G) and homogeneously dissolving the mixture at from 60 to 100° C. to form an oil phase portion; and homogeneously mixing the aqueous phase portion with the oil phase portion, followed by cooling.

The skin cosmetic of the present invention has a pH of preferably from 5.5 to 8.5, more preferably from 6.0 to 8.0, further preferably from 6.5 to 7.8, at 25° C. from the viewpoint of forming a stable lamellar α-gel structure in the cosmetic. In the present invention, the pH is determined by directly measuring the pH of a sample at 25° C. using a pH meter (F-52, manufactured by Horiba, Ltd.).

The skin cosmetic of the present invention can be prepared as, for example, a skin lotion, an emulsion, a cream, a gel, or a serum and is more preferably used as an emulsion or a cream. Also, the skin cosmetic of the present invention can be used as a sheet-shaped cosmetic in which a sheet-shaped base material such as woven cloth or nonwoven cloth is impregnated with the skin cosmetic of the present invention or the skin cosmetic of the present invention is applied to such a base material.

The skin cosmetic of the present invention can be applied, for use, to the skin, preferably the skin except for the scalp, more preferably any of the face, the body, limbs, and the like.

The skin cosmetic of the present invention can moisturize the skin by application to the skin, and can improve aesthetic appearance in such a way to brighten skin color or conceal blemishes, by using preferably titanium oxide, talc, iron oxide, silica, or (lauryl methacrylate/sodium methacrylate) crosspolymer, more preferably titanium oxide, as the powder.

As for the aforementioned embodiments, the present invention further discloses the following compositions and methods for using the same and methods for producing the same.

<1> A skin cosmetic containing the following components (A), (B), (C), (D), (E), and (F):
(A) 0.5 to 6 mass % of a linear saturated fatty acid having 12 to 22 of carbon atom,
(B) 0.010 to 5 mass % of an organic base,
(C) 0.010 to 1 mass % of an inorganic base,
(D) 0.5 to 6 mass % of a linear saturated alcohol having 12 to 22 of carbon atom,
(E) 0.05 to 9 mass % of a powder, and
(F) water, wherein
the mass ratio of the component (E) to the total amount of the components (A) and (D) [(A)+(D)] is (E)/[(A)+(D)]=from 0.01 to 5.

<2> A skin cosmetic comprising the following components (A), (B), (C), (D), (E), and (F):
(A) 0.5 to 6 mass % of a linear saturated fatty acid having 12 to 22 of carbon atom,
(B) 0.010 to S mass % of an organic base,
(C) 0.010 to 1 mass % of an inorganic base,
(D) 0.5 to 6 mass % of a linear saturated alcohol having 12 to 22 of carbon atom,
(E) 0.05 to 9 mass % of a powder, and
(F) water, wherein
the component (D) contains at least a linear saturated alcohol having 12 to 20 of carbon atom, and
the mass ratio of the component (E) to the total amount of the components (A) and (D) [(A)+(D)] is (E)/[(A)+(D)]=from 0.01 to 5.

<3> A skin cosmetic containing the following components (A), (B), (C), (D), (E), and (F):
(A) 0.5 to 6 mass % of a linear saturated fatty acid having 12 to 22 of carbon atom,
(B) 0.010 to 5 mass % of an organic base,
(C) 0.010 to 1 mass % of an inorganic base,
(D) 0.5 to 6 mass % of a linear saturated alcohol having 12 to 22 of carbon atom,
(E) 0.05 to 9 mass % of a powder, and
(F) 50 to 98 mass % of water, wherein the mass ratio of the component (E) to the total amount of the components (A) and (D) [(A)+(D)] is (E)/[(A)+(D)]=from 0.01 to 5.

<4> A skin cosmetic containing the following components (A), (B), (C), (D), (E), and (F):
(A) 0.5 to 6 mass % of a linear saturated fatty acid having 12 to 22 of carbon atom,
(B) 0.010 to 5 mass % of an organic base,
(C) 0.010 to 1 mass % of an inorganic base,
(D) 0.5 to 6 mass % of a linear saturated alcohol having 12 to 22 of carbon atom,
(E) 0.05 to 9 mass % of a powder, and
(F) 50 to 98 mass % of water, wherein
the component (D) contains at least a linear saturated alcohol having 12 to 20 of carbon atom, and
the mass ratio of the component (E) to the total amount of the components (A) and (D) [(A)+(D)] is (E)/[(A)+(D)]=from 0.01 to 5.

<5> The skin cosmetic according to any one of <1> to <4>, further containing (G) a nonionic surfactant, wherein the content thereof in the whole composition is preferably 0.05 mass % or more, more preferably 0.1 mass % or more further preferably 0.2 mass % or more, and is preferably 2 mass % or less, more preferably 1.5 mass % or less, further preferably 1 mass % or less.

<6> The skin cosmetic according to <5>, wherein the nonionic surfactant (G) is preferably one or more selected from the group consisting of an ethylene glycol fatty acid ester, a polyethylene glycol fatty acid ester, a polyalkylene glycol alkyl ether, a polyethylene glycol hydrogenated castor oil, a propylene glycol fatty acid ester, a monoglycerin monofatty acid ester, a monoglycerin difatty acid ester, a glycerin alkyl ether, a sorbitan fatty acid ester, a fatty acid alkanolamide, and a fatty acid dialkanolamide, more preferably a polyalkylene glycol alkyl ether, further preferably a polyalkylene glycol alkyl ether having an alkyl group having 12 to 22 of carbon atom, still further preferably a polyalkylene glycol alkyl ether having an alkyl group having 12 to 18 of carbon atom.

<7> The skin cosmetic according to <5> or <6>, wherein the nonionic surfactant (G) has an HLB of preferably from 8 to 19, more preferably from 10 to 16.

<8> The skin cosmetic according to any one of <5> to <7>, wherein the nonionic surfactant (G) is ceteareth-20.

<9> The skin cosmetic according to any one of <1> to <8>, wherein the component (A) is preferably one or two or more selected from the group consisting of lauric acid, myristic acid, palmitic acid, stearic acid, and behenic acid, more preferably palmitic acid or stearic acid <10> The skin cosmetic according to any one of <1> to <9>, wherein the content of the component (A) in the whole composition is preferably 1 mass % or more, more preferably 1.5 mass % or more, and is preferably 4 mass % or less, more preferably 3.8 mass % or less.

<11> The skin cosmetic according to any one of <1> to <10>, wherein the component (B) preferably contains at least any one or more of alkylamines selected from the group consisting of methylamine, ethylamine, propylamine, butylamine, hexylamine, dimethylamine, and diethylamine; alkanolamines selected from the group consisting of monoethanolamine, diethanolamine, triethanolamine, 2-amino-2-hydroxymethyl-1,3-propanediol, N-methyl-diethanolamine, N,N-dimethyl monoethanolamine, and aminomethyl propanol; and basic amino acids selected from the group consisting of lysine, histidine, and arginine.

<12> The skin cosmetic according to any one of <1> to <11>, wherein the component (B) is preferably an alkanolamine having an alkyl group having 1 to 6 of carbon atom or a basic amino acid having 1 to 6 of carbon atom, more preferably an alkanolamine having an alkyl group having 3 to 6 of carbon atom or a basic amino acid having 3 to 6 of carbon atom, further preferably a basic amino acid.

<13> The skin cosmetic according to any one of <1> to <12>, wherein the component (B) is preferably aminomethyl propanol or arginine, more preferably arginine, wherein the arginine is preferably L-arginine.

<14> The skin cosmetic according to any one of <1> to <13>, wherein the content of the component (B) in the whole composition is preferably 0.02 mass % or more, more preferably 0.05 mass % or more, further preferably 0.1 mass % or more, and is preferably 2 mass % or less, more preferably 0.8 mass % or less, further preferably 0.4 mass % or less.

<15> The skin cosmetic according to any one of <1> to <14>, wherein the component (C) is preferably sodium hydroxide or potassium hydroxide.

<16> The skin cosmetic according to any one of <1> to <15>, wherein the content of the component (C) in the whole composition is preferably 0.04 mass % or more, more preferably 0.08 mass % or more, and is preferably 0.3 mass % or less, more preferably 0.25 mass %; or less.

<17> The skin cosmetic according to any one of <1> to <16>, wherein the component (D) is preferably a linear saturated alcohol having 14 to 22 of carbon atom, more preferably a linear saturated alcohol having 16 to 22 of carbon atom, further preferably a linear saturated alcohol having 16 to 20 of carbon atom.

<18> The skin cosmetic according to any one of <1> to <17>, wherein the component (D) is preferably one or more selected from the group consisting of myristyl alcohol, cetyl alcohol, stearyl alcohol, and behenyl alcohol, more preferably one or more selected from the group consisting of cetyl alcohol and stearyl alcohol, and further preferably contains cetyl alcohol and stearyl alcohol.

<19> The skin cosmetic according to any one of <1> to <18>, wherein the content of the component (D) in the whole composition is preferably 1 mass % or more, more preferably 1.3 mass % or more, and is preferably 5.5 mass % or less, more preferably 5.2 mass % or less.

<20> The skin cosmetic according to any one of <1> to <19>, wherein the component (E) preferably contains at least one selected from the group consisting of titanium oxide, talc, iron oxide, silica, and (lauryl methacrylate/sodium methacrylate) crosspolymer, and more preferably contains titanium oxide.

<21> The skin cosmetic according to any one of <1> to <20>, wherein the component (E) has a volume-average particle size of preferably 0.005 μm or larger, more preferably 0.01 μm or larger, further preferably 0.05 μm or larger, still further preferably 0.07 μm or larger, particularly preferably 0.1 μm or larger, and of preferably 10 μm or smaller, more preferably 5 μm or smaller, further preferably 3 μm or smaller, still further preferably 1 μm or smaller, particularly preferably 0.5 μm or smaller.

<22> The skin cosmetic according to any one of <1> to <20>, wherein the component (E) has a volume-average particle size of preferably 0.005 μm or larger, more preferably 0.007 μm or larger, further preferably 0.01 μm or larger, and of preferably 0.2 μm or smaller, more preferably 0.1 μm or smaller, further preferably 0.05 μm or smaller.

<23> The skin cosmetic according to any one of <1> to <22>, wherein the component (E) preferably has undergone hydrophilizing treatment or hydrophobizing treatment, more preferably metallic soap treatment, silicone treatment, or amino acid treatment, further preferably treatment with fatty acid zinc salt, fatty acid magnesium salt, fatty acid aluminum salt, dimethylsiloxane, trimethoxycaprylylsilane, triethoxycaprylylsilane, methyl hydrogen siloxane, or sodium stearoyl glutamate.

<24> The skin cosmetic according to any one of <1> to <23>, wherein the content of the component (E) in the whole composition is preferably 0.08 mass % or more, more preferably 0.1 mass % or more, further preferably 0.4 mass % or more, and is preferably 5 mass % or less, more preferably 4 mass % or less, further preferably 2 mass % or less.

<25> The skin cosmetic according to any one of <1> to <23>, wherein the content of the component (E) in the whole composition is preferably 1 mass % or more, more preferably 1.5 mass % or more, further preferably 2.5 mass % or more, still further preferably 3 mass % or more, and is preferably 7 mass % or less, more preferably 6 mass % or less, further preferably 5 mass % or less, still further preferably 4.5 mass % or less.

<26> The skin cosmetic according to any one of <1> to <25>, wherein the content of water as the component (F) in the whole composition is preferably 50 mass % or more, more preferably 60 mass % or more, and is preferably 96 mass % or less, more preferably 95 mass % or less.

<27> The skin cosmetic according to any one of <1> to <25>, wherein the content of water as the component (F) in the whole composition is preferably 50 mass % or more, more preferably 60 mass % or more, and is preferably 98 mass % or less, more preferably 96 mass % or less.

<28> The skin cosmetic according to any one of <3> to <27>, wherein the mass ratio of the total amount of the components (A) and (D) [(A)+(D)] to the component (G), [(A)+(D)]/G, is preferably 2 or more, more preferably 3 or more, further preferably 4 or more, and is preferably 30 or less, more preferably 20 or less, further preferably 10 or less.

<29> The skin cosmetic according to any one of <1> to <28>, wherein the total amount of the components (A) and (D), (A)+(D), in the whole composition is preferably 1 mass % or more, more preferably 2 mass % or more, further preferably 3 mass % or more, and is preferably 12 mass % or less, more preferably 9.5 mass % or less, further preferably 8 mass % or less.

<30> The skin cosmetic according to any one of <1> to <29>, wherein the mass ratio of the component (A) to the total amount of the components (A) and (D) [(A)+(D)], (A)/[(A)+(D)], is preferably 0.2 or more, more preferably 0.25 or more, further preferably 0.27 or more, still further preferably 0.30 or more, and is preferably 0.7 or less, more preferably 0.65 or less, further preferably 0.60 or less, still further preferably 0.55 or less.

<31> The skin cosmetic according to any one of <1> to <30>, wherein the mass ratio of the component (E) to the total amount of the components (A) and (D) [(A)+(D)], (E)/[(A)+(D)], is preferably 0.05 or more, more preferably 0.07 or more, further preferably 0.1 or more, and is preferably 4 or less, more preferably 3 or less, further preferably 1 or less.

<32> The skin cosmetic according to any one of <1> to <31>, wherein the molar ratio of the component (B) to the total amount of the components (B) and (C) [(B)+(C)], (B)/[(B)+(C)] preferably from 5 to 75, more preferably from 8 to 70, further preferably from 10 to 65.

<33> The skin cosmetic according to any one of <1> to <32>, wherein the molar ratio of the total amount of the components (B) and (C) [(B)+(C))] to the component (A), [(B)+(C)]/(A), is preferably from 10 to 110, more preferably from 20 to 100, further preferably from 30 to 90.

<34> The skin cosmetic according to any one of <1> to <33>, optionally further containing an ultraviolet absorber as a component (I).

<35> The skin cosmetic according to <34>, wherein the ultraviolet absorber is preferably oil-soluble and is more preferably a benzoic acid ultraviolet absorber, an anthranilic acid ultraviolet absorber, a salicylic acid ultraviolet absorber, a cinnamic acid ultraviolet absorber, a benzophenone ultraviolet absorber, or a triazine ultraviolet absorber.

<36> The skin cosmetic according to <34> or <35>, wherein the ultraviolet absorber is preferably at least one selected from the group consisting of a benzoic acid ultraviolet absorber, a salicylic acid ultraviolet absorber, a cinnamic acid ultraviolet absorber, a benzophenone ultraviolet absorber, and a triazine ultraviolet absorber, more preferably at least one or more selected from the group consisting of a salicylic acid ultraviolet absorber, a cinnamic acid ultraviolet absorber, and a benzophenone ultraviolet absorber, further preferably at least two or more selected from the group consisting of a salicylic acid ultraviolet absorber, a cinnamic acid ultraviolet absorber, and a benzophenone ultraviolet absorber.

<37> The skin cosmetic according to <35> or <36>, wherein the benzoic acid ultraviolet absorber is preferably p-aminobenzoic acid, or diethylamino hydroxybenzoyl hexyl benzoate, more preferably diethylamino hydroxybenzoyl hexyl benzoate.

<38> The skin cosmetic according to <35>, wherein the anthranilic acid ultraviolet absorber is preferably homomenthyl-N-acetyl anthranilate.

<39> The skin cosmetic according to <35> or <36>, wherein the salicylic acid ultraviolet absorber is preferably homomenthyl salicylate or octyl salicylate.

<40> The skin cosmetic according to <35> or <36>, wherein the cinnamic acid ultraviolet absorber is preferably octyl cinnamate or 2-ethylhexyl-p-methoxy cinnamate, more preferably 2-ethylhexyl-p-methoxy cinnamate.

<41> The skin cosmetic according to <35> or <36>, wherein the benzophenone ultraviolet absorber is preferably 2-hydroxy-4-methoxybenzophenone.

<42> The skin cosmetic according to <35> or <36>, wherein the triazine ultraviolet absorber is preferably 2,4,6-tris[4-(2-ethylhexyloxycarbonyl)anilino]-1,3,5-triazine or 2,4-bis-[{4-(2-ethylhexyloxy)-2-hydroxy}-phenyl]-6-(4-methoxyphenyl)-1,3,5-triazine.

<43> The skin cosmetic according to <34>, wherein the ultraviolet absorber is preferably 4-tert-butylbenzoyl(4-methoxybenzoyl)methane or 2-ethylhexyl 2-cyano-3,3-diphenylacrylate.

<44> The skin cosmetic according to any one of <34> to <43>, wherein the content of the component (I) in the whole composition is preferably 0.1 mass % or more, more preferably 0.5 mass % or more, further preferably 3 mass % or more, still further preferably 5 mass % or more, and is preferably 30 mass % or less, more preferably 20 mass % or less, further preferably 18 mass % or less, still further preferably 15 mass % or less.

<45> The skin cosmetic according to any one of <1> to <44>, wherein the skin cosmetic has a pH of preferably from 5.5 to 8.5, more preferably from 6.0 to 8.0, further preferably from 6.5 to 7.8, at 25° C.

<46> The skin cosmetic according to any one of <1> to <45>, wherein the content of an anionic surfactant in the whole composition is preferably 1 mass % or less, more preferably 0.5 mass % or less, further preferably 0.3 mass % or less, still further preferably 0.1 mass % or less.

<47> The skin cosmetic according to any one of <1> to <46>, wherein the content of a solid fat other than the components (A) and (D) in the whole composition is preferably 5 mass % or less, more preferably 3 mass % or less, further preferably 1 mass % or less, still further preferably 0.5 mass % or less.

<48> A method for using a skin cosmetic, including using a skin cosmetic according to any one of <1> to <47> to the skin, preferably applying a skin cosmetic according to any one of <1> to <47> to the skin, preferably the skin except for the scalp, more preferably any of the face, the body, limbs, and the like.

<49> A method for producing a skin cosmetic according to any one of <1> to <4> and <9> to <47>, including steps 1 to 3:
step 1: the step of mixing the components (B), (C), and (F) and homogeneously dissolving the mixture at from 60 to 100° C. to form an aqueous phase portion,
step 2: the step of mixing the components (A), (D), and (E) and homogeneously dissolving the mixture at from 60 to 100° C. to form an oil phase portion, and
step 3: the step of homogeneously mixing the aqueous phase portion obtained in step 1 with the oil phase portion obtained in step 2 and cooling the mixture to preferably from 20 to 45° C., more preferably from 25 to 40° C., further preferably from 30 to 35° C.

<50> A method for producing a skin cosmetic according to any one of <1> to <4> and <9> to <47>, including steps 1 to 3:
step 1: the step of mixing the components (C) and (F) and homogeneously dissolving the mixture at from 60 to 100° C. to form an aqueous phase portion,
step 2: the step of mixing the components (A), (B), (D), and (E) and homogeneously dissolving the mixture at from 60 to 100° C. to form an oil phase portion, and
step 3: the step of homogeneously mixing the aqueous phase portion obtained in step 1 with the oil phase portion obtained in step 2 and cooling the mixture to preferably from 20 to 45° C., more preferably from 25 to 40° C., further preferably from 30 to 35° C.

<51> A method for producing a skin cosmetic according to any one of <5> to <8>, including steps 1 to 3:
step 1: the step of mixing the components (B), (C), and (F) and homogeneously dissolving the mixture at from 60 to 100° C. to form an aqueous phase portion,
step 2: the step of mixing the components (A), (D), (E), and (G) and homogeneously dissolving the mixture at from 60 to 100° C. to form an oil phase portion, and
step 3: the step of homogeneously mixing the aqueous phase portion obtained in step 1 with the oil phase portion obtained in step 2 and cooling the mixture to preferably from 20 to 45° C., more preferably from 25 to 40° C., further preferably from 30 to 35° C.

<52> A method for producing a skin cosmetic according to any one of <5> to <8>, including steps 1 to 3: step 1: the step of mixing the components (C) and (F) and homogeneously dissolving the mixture at from 60 to 100° C. to form an aqueous phase portion,
step 2: the step of mixing the components (A), (B), (D), (E), and (G) and homogeneously dissolving the mixture at from 60 to 100° C. to form an oil phase portion, and
step 3: the step of homogeneously mixing the aqueous phase portion obtained in step 1 with the oil phase portion obtained in step 2 and cooling the mixture to preferably from 20 to 45° C., more preferably from 25 to 40° C., further preferably from 30 to 35° C.

<53> A moisturizing method comprising applying a skin cosmetic according to any one of <1> to <47> to the skin.

<54> A method for improving aesthetic appearance, comprising applying a skin cosmetic according to any one of <1> to <47> to the skin.

EXAMPLES

Production Example 1

(Production of (Lauryl Methacrylate/Sodium Methacrylate) Crosspolymer)

In a beaker, 82 g of lauryl methacrylate, 3 g of methacrylic acid, 15 g of ethylene glycol dimethacrylate, and 2 g of lauroyl peroxide were placed, and the mixture was dissolved by mixing and stirring. 400 g of ion-exchange water containing 0.75 g of sodium N-stearoyl-N-methyltaurine (SMT) dissolved therein was added thereto and dispersed with a homo mixer until the particle size reached 2.2 μm. This dispersion was poured into a 4-neck flask, which was then purged with nitrogen for 30 minutes with stirring. The internal temperature of the flask was raised to 80° C. in an oil bath. After this temperature reached 80° C., polymerization was carried out for 5 hours. Then, the reaction product was neutralized by the dropwise addition of 3.9 g of 1 N NaOH. The polymerized particle dispersion was freeze-dried, and the particles were recovered therefrom to obtain a resin powder.

Examples 1 to 32 and Comparative Examples 1 to 14

Skin cosmetics were produced according to the composition shown in Tables 1 to 3 and evaluated for the absence of stickiness upon application, the presence or absence of α-type structure formation in a coating film, the moisture-confining properties (moisturizing properties) of the coating film, the uniform dispersibility of the powder in the coating film, the brightness of the coating film, and less likelihood of the coating film to come off against friction. The results are also shown in Tables 1 to 3.

(Production Method)

The aqueous phase components including the components (B), (C), and (F) were dissolved by stirring at 70 to 80° C. to form an aqueous phase portion. Next, the oil phase components including the components (A), (D), (E), and (G) were dissolved by stirring at 70 to 80° C. to form an oil phase portion. The oil phase portion was added to the aqueous phase portion with stirring at 70 to 80° C., and the mixture was cooled to room temperature (30° C.) with further stirring to produce a skin cosmetic (oil-in-water emulsion cosmetic).

(Evaluation Method)

(1) Absence of Stickiness Upon Application:

Five expert panelists used 2 mg/cm² of each cosmetic on their forearms and conducted sensory evaluation on the absence of stickiness according to the following criteria, and an average of the scores was determined.
5: The absence of stickiness was strongly felt.
4: The absence of stickiness was felt.
3: The absence of stickiness was slightly felt.
2: Stickiness was felt.
1: Stickiness was strongly felt.

(2) Presence or Absence of α-Type Structure Formation in Coating Film:

Each cosmetic was applied at a thickness of 0.1 mm to the surface of black artificial leather (Sela Nubuck Black, manufactured by Okamoto Kaseihin Co., Ltd.) using an applicator (manufactured by Yoshimitsu Seiki Co., Ltd.) and dried at room temperature for 1 day. The dried film was fractionated, and the phase state of the dried film was analyzed by wide-angle X-ray diffraction measurement. In the obtained X-ray diffraction profile, the presence or absence of a diffraction peak at approximately 21.5° was observed, and the results were indicated as follows.

α type: A film was formed and had an α-type structure.
–: No film was formed, or a film was formed but contained a non-α-type structure.

(3) Moisture-Confining Properties (Moisturizing Properties) of Coating Film:

Each cosmetic was applied at 0.01 mL/cm² to 5C quantitative filter paper (manufactured by Toyo Roshi Kaisha, Ltd., ADVANTEC FILTER PAPER 5C) and left standing at 20° C. for 24 hours in a 20% RH environment. A portion of this filter paper was cut out and placed on a 40-mL vial (Pierce Vial CV-400, manufactured by AS ONE Corp.; the lid has an opening of 17.3 mm in diameter) to cover the top of the vial therewith. A given amount of water was added to the vial, and the resulting vial was left standing at 20° C. for 24 hours in a 20% RH environment. The amount of water decreased was measured.

The mass before storage was defined as m1; the mass after 24 hours was defined as m2; the amount of water loss in the case of cosmetic-unapplied filter paper was defined as W (g); and the amount of water loss in the case where the cosmetic of each Example or Comparative Example was applied to the filter paper was defined as S (g). The rate of suppression of water loss (%) was determined according to the following expressions:

Amount of water loss $W$ (g)=$Wm1-Wm2$

Amount of water loss $S$ (g)=$Sm1-Sm2$

Rate of suppression of water loss (%)=$(W$ (g)$-S$ (g)$)/W$ (g)$\times 100$

A higher numeric value represents better moisture-confining properties (moisturizing properties).

(4) Uniform Dispersibility of Powder in Coating Film:

Each cosmetic was applied at a thickness of 0.1 mm to the surface of black artificial leather (Sela Nubuck Black, manufactured by Okamoto Kaseihin Co., Ltd.) using an applicator (manufactured by Yoshimitsu Seiki Co., Ltd.) and dried at room temperature for 1 day. The resulting film was observed under a microscope (×10) and evaluated according to the following criteria:

5: The powder was very uniformly dispersed.
4: The powder was uniformly dispersed.
3: The powder was almost uniformly dispersed.
2: The powder was hardly uniformly dispersed.
1: The powder was not uniformly dispersed.

(5) Brightness of Coating Film:

Five expert panelists used 2 mg/cm² of each cosmetic on their forearms and conducted sensory evaluation on change in the brightness of skin color according to the following criteria, and an average of the scores was determined.

5: The skin color became very bright.
4: The skin color became bright.
3: The skin color became slightly bright.
2: The skin color hardly became bright.
1: The skin color did not become bright.

(6) Less Likelihood of Coating Film to Come Off Against Friction:

Each cosmetic was applied at a thickness of 0.1 mm to the surface of black artificial leather (Sela Nubuck Black, 5 cm×15 cm, manufactured by Okamoto Kaseihin Co., Ltd.) using an applicator (manufactured by Yoshimitsu Seiki Co., Ltd.) and dried for 1 day. Then, the resulting film was reciprocated five times with a stroke of 5 cm (5 cm/s) under a load of 50 g/cm² using a surface property tester (HEIDON, manufactured by Sohgoh Keiso Co., Ltd.). Five expert panelists visually observed the degree of change in appearance and evaluated less likelihood of the coating film to come off and change in the brightness of the coating film between before and after friction, according to the following criteria:

5: The coating film did not come off, and no change was seen in the brightness.
4: The coating film mostly remained, and almost no change was seen in the brightness.
3: The coating film slightly remained, and the brightness was not much reduced.
2: The coating film came off, and the brightness was reduced.
1: Most of the coating film came off, and the brightness was largely reduced.

TABLE 1

| | Component (mass %) | Example | | | | | | |
|---|---|---|---|---|---|---|---|---|
| | | 1 | 2 | 3 | 4 | 5 | 6 | 7 |
| A | Stearic acid | 0.5 | 0.5 | 6 | 2 | 3 | 3.5 | 3 |
| B | L-arginine | 0.01 | 0.01 | 1 | 0.03 | 0.03 | 0.7 | 0.08 |
| C | Sodium hydroxide | 0.015 | 0.015 | 0.4 | 0.05 | 0.05 | 0.22 | 0.05 |
| D | Cetostearyl alcohol | 1.4 | 0.5 | 5.2 | 5 | 5 | 4 | 5 |
| E | Titanium oxide*1 | 6 | 0.05 | 0.12 | 1 | 0.5 | 0.09 | 0.09 |
| G | Ceteareth-20 (HLB 16.1) | 0.15 | 0.07 | 1.6 | 0.5 | 0.5 | 0.5 | 0.5 |
| F | Water | Balance | Balance | Balance | Balance | Balance | Balance | Balance |
| | Total | 100 | 100 | 100 | 100 | 100 | 100 | 100 |
| | A+D | 1.9 | 1 | 11.2 | 7 | 8 | 7.5 | 8 |
| | A/(A+D) Mass ratio | 0.26 | 0.50 | 0.54 | 0.29 | 0.38 | 0.47 | 0.38 |
| | B/(B+C) Molar ratio | 13.3 | 13.3 | 36.4 | 12.1 | 12.1 | 42.2 | 26.8 |
| | (B+C)/A Molar ratio | 24.6 | 24.6 | 74.6 | 20.2 | 13.5 | 77.4 | 16.2 |
| | E/(A+D) Mass ratio | 3.16 | 0.05 | 0.011 | 0.14 | 0.06 | 0.012 | 0.011 |
| | Absence of stickiness upon application | 5.0 | 5.0 | 3.0 | 4.0 | 4.0 | 4.0 | 4.0 |
| | Presence or absence of α-type structure formation in coating film | α type | α type | α type | α type | α type | α type | α type |

TABLE 1-continued

| | | | | | | | |
|---|---|---|---|---|---|---|---|
| Moisture-confining properties (moisturizing properties) of coating film | 20 | 19 | 51 | 40 | 42 | 41 | 44 |
| Uniform dispersibility of powder in coating film | 3 | 4 | 4 | 5 | 5 | 5 | 5 |
| Brightness of coating film | 5.0 | 3.0 | 4.0 | 5.0 | 5.0 | 4.0 | 4.0 |
| Less likelihood of coating film to come off against friction | 3 | 3 | 5 | 5 | 5 | 5 | 5 |

| | Component (mass %) | Example 8 | 9 | 10 | 11 | 12 | 13 | 14 |
|---|---|---|---|---|---|---|---|---|
| A | Stearic acid | 3.5 | 2 | 2 | 2 | 2 | 2 | 2 |
| B | L-arginine | 0.45 | 0.14 | 0.14 | 0.14 | 0.14 | 0.14 | 0.14 |
| C | Sodium hydroxide | 0.22 | 0.15 | 0.15 | 0.15 | 0.15 | 0.15 | 0.15 |
| D | Cetostearyl alcohol | 4 | 2 | 2 | 2 | 2 | 2 | 2 |
| E | Titanium oxide*1 | 8.5 | 0.5 | 0.5 | 0.08 | 0.05 | 2.5 | 5 |
| G | Ceteareth-20 (HLB 16.1) | 0.5 | 0.5 | | 0.5 | 0.5 | 0.5 | 0.5 |
| F | Water | Balance | Balance | Balance | Balance | Balance | Balance | Balance |
| | Total | 100 | 100 | 100 | 100 | 100 | 100 | 100 |
| | A+D | 7.5 | 4 | 4 | 4 | 4 | 4 | 4 |
| | A/(A+D) Mass ratio | 0.47 | 0.50 | 0.50 | 0.50 | 0.50 | 0.50 | 0.50 |
| | B/(B+C) Molar ratio | 31.9 | 17.6 | 17.6 | 17.6 | 17.6 | 17.6 | 17.6 |
| | (B+C)/A Molar ratio | 65.7 | 64.8 | 64.8 | 64.8 | 64.8 | 64.8 | 64.8 |
| | E/(A+D) Mass ratio | 1.13 | 0.13 | 0.13 | 0.020 | 0.013 | 0.625 | 1.250 |
| | Absence of stickiness upon application | 4.0 | 5.0 | 5.0 | 5.0 | 5.0 | 5.0 | 5.0 |
| | Presence or absence of α-type structure formation in coating film | α type | α type | α type | α type | α type | α type | α type |
| | Moisture-confining properties (moisturizing properties) of coating film | 38 | 38 | 38 | 39 | 40 | 35 | 34 |
| | Uniform dispersibility of powder in coating film | 4 | 5 | 4 | 5 | 5 | 5 | 4 |
| | Brightness of coating film | 5.0 | 5.0 | 4.0 | 4.0 | 3.0 | 5.0 | 5.0 |
| | Less likelihood of coating film to come off against friction | 5 | 5 | 5 | 5 | 5 | 5 | 5 |

*1: TIPAQUE CR-50 (manufactured by Ishihara Sangyo Kaisha, Ltd.), average particle size: 250 nm, silica alumina treatment

TABLE 2

| | Component (mass %) | Example 15 | 16 | 17 | 18 | 19 | 20 | 21 | 22 | 23 |
|---|---|---|---|---|---|---|---|---|---|---|
| A | Myrislic acid | | 0.5 | | | | | | | |
| | Palmilic acid | | | 0.5 | | | | | | |
| | Stearic acid | 2 | 1.5 | 1.5 | 1.5 | 2 | 2 | 2 | 2 | 2 |
| | Behenic acid | | | | 0.5 | | | | | |
| B | L-arginine | 0.14 | 0.14 | 0.14 | 0.14 | | | 0.07 | 0.07 | 0.14 |
| | 2-Amino-2-methyl-1-propanol | | | | | 0.14 | 0.07 | | | |
| | Triethanolamine | | | | | | | 0.07 | | |
| | 2-Amino-2-hydroxymethyl-1,3-propanediol | | | | | | | | 0.07 | |
| C | Sodium hydroxide | 0.15 | 0.15 | 0.15 | 0.15 | 0.15 | 0.15 | 0.15 | 0.15 | 0.15 |
| D | Myristyl alcohol | | | | | | | | | 0.5 |
| | Cetyl alcohol | 1.2 | 1.2 | 1.2 | 1.2 | 1.2 | 1.2 | 1.2 | 1.2 | 1 |
| | Stearyl alcohol | 0.8 | 0.8 | 0.8 | 0.8 | 0.8 | 0.8 | 0.8 | 0.8 | 0.5 |
| | Behenyl alcohol | | | | | | | | | |
| E | Titanium oxide*1 | 0.6 | 0.6 | 0.6 | 0.6 | 0.6 | 0.6 | 0.6 | 0.6 | 0.6 |
| | Fine titanium oxide particle*2 | | | | | | | | | |
| | (Lauryl methacrylate/sodium methacrylate) crosspolymer*3 | | | | | | | | | |
| | Silica*4 | | | | | | | | | |
| | Iron oxide*5 | | | | | | | | | |
| | Synthetic phlogopite*6 | | | | | | | | | |
| | Talc*7 | | | | | | | | | |
| G | Ceteareth-20 (HLB 16.1) | 0.5 | 0.5 | 0.5 | 0.5 | 0.5 | 0.5 | 0.5 | 0.5 | 0.5 |
| F | Water | Balance | Balance | Balance | Balance | Balance | Balance | Balance | Balance | Balance |
| | Total | 100 | 100 | 100 | 100 | 100 | 100 | 100 | 100 | 100 |
| | A+D | 4 | 4 | 4 | 4 | 4 | 4 | 4 | 4 | 4 |
| | A/(A+D) Mass ratio | 0.50 | 0.50 | 0.50 | 0.50 | 0.50 | 0.50 | 0.50 | 0.50 | 0.50 |
| | B/(B+C) Molar ratio | 17.6 | 17.6 | 17.6 | 17.6 | 29.5 | 24.0 | 18.8 | 20.7 | 17.6 |
| | (B+C)/A Molar ratio | 64.8 | 61.0 | 63.0 | 67.5 | 75.7 | 70.2 | 65.7 | 67.3 | 64.8 |
| | E/(A+D) Mass ratio | 0.15 | 0.15 | 0.15 | 0.15 | 0.15 | 0.15 | 0.15 | 0.15 | 0.15 |
| | Absence of stickiness upon application | 5 | 4 | 5 | 5 | 5 | 5 | 5 | 5 | 4 |
| | Presence or absence of α-type structure formation in coating film | α-type | α-type | α-type | α-type | α-type | α-type | α-type | α-type | α-type |
| | Moisture-confining properties (moisturizing properties) of coating film | 39 | 35 | 37 | 36 | 37 | 36 | 35 | 36 | 35 |

TABLE 2-continued

| | 24 | 25 | 26 | 27 | 28 | 29 | 30 | 31 | 32 |
|---|---|---|---|---|---|---|---|---|---|
| Uniform dispersibility of powder in coating film | 5.0 | 5.0 | 5.0 | 5.0 | 5.0 | 5.0 | 5.0 | 5.0 | 5.0 |
| Brightness of coating film | 5 | 5 | 5 | 5 | 5 | 5 | 5 | 5 | 5 |
| Less likelihood of coating film to come off against friction | 5.0 | 4.0 | 5.0 | 5.0 | 5.0 | 5.0 | 5.0 | 5.0 | 5.0 |

| | Component (mass %) | Example 24 | 25 | 26 | 27 | 28 | 29 | 30 | 31 | 32 |
|---|---|---|---|---|---|---|---|---|---|---|
| A | Myristic acid | | | | | | | | | |
| | Palmitic acid | | | | | | | | | |
| | Stearic acid | 2 | 2 | 2 | 2 | 2 | 2 | 2 | 2 | 2 |
| | Behenic acid | | | | | | | | | |
| B | L-arginine | 0.14 | 0.14 | 0.14 | 0.14 | 0.14 | 0.14 | 0.14 | 0.14 | 0.14 |
| | 2-Amino-2-methyl-1-propanol | | | | | | | | | |
| | Triethanolamine | | | | | | | | | |
| | 2-Amino-2-hydroxymethyl-1,3-propanediol | | | | | | | | | |
| C | Sodium hydroxide | 0.15 | 0.15 | 0.15 | 0.15 | 0.15 | 0.15 | 0.15 | 0.15 | 0.15 |
| D | Myristyl alcohol | | | | | | | | | |
| | Cetyl alcohol | 1 | 1.2 | 1.2 | 1.2 | 1.2 | 1.2 | 1.2 | 1.2 | 1.2 |
| | Stearyl alcohol | 0.5 | 0.8 | 0.8 | 0.8 | 0.8 | 0.8 | 0.8 | 0.8 | 0.8 |
| | Behenyl alcohol | 0.5 | | | | | | | | |
| E | Titanium oxide*1 | 0.6 | | | | 0.5 | | | 0.3 | 0.3 |
| | Fine titanium oxide particle*2 | | 0.6 | | | | | | 0.3 | |
| | (Lauryl methacrylate/sodium methacrylate) crosspolymer*3 | | | 0.6 | | | | | | 0.3 |
| | Silica*4 | | | | 0.6 | | | | | |
| | Iron oxide*5 | | | | | 0.1 | | | | |
| | Synthetic phlogopite*6 | | | | | | 0.6 | | | |
| | Talc*7 | | | | | | | 0.6 | | |
| G | Ceteareth-20 (HLB 16.1) | 0.5 | 0.5 | 0.5 | 0.5 | 0.5 | 0.5 | 0.5 | 0.5 | 0.5 |
| F | Water | Balance | Balance | Balance | Balance | Balance | Balance | Balance | Balance | Balance |
| | Total | 100 | 100 | 100 | 100 | 100 | 100 | 100 | 100 | 100 |
| | A+D | 4 | 4 | 4 | 4 | 4 | 4 | 4 | 4 | 4 |
| | A/(A+D) Mass ratio | 0.50 | 0.50 | 0.50 | 0.50 | 0.50 | 0.50 | 0.50 | 0.50 | 0.50 |
| | B/(B+C) Molar ratio | 17.6 | 17.6 | 17.6 | 17.6 | 17.6 | 17.6 | 17.6 | 17.6 | 17.6 |
| | (B+C)/A Molar ratio | 64.8 | 64.8 | 64.8 | 64.8 | 64.8 | 64.8 | 64.8 | 64.8 | 64.8 |
| | E/(A+D) Mass ratio | 0.15 | 0.15 | 0.15 | 0.15 | 0.15 | 0.15 | 0.15 | 0.15 | 0.15 |
| | Absence of stickiness upon application | 5 | 5 | 5 | 5 | 5 | 5 | 5 | 5 | 5 |
| | Presence or absence of α-type structure formation in coating film | α-type | α-type | α-type | α-type | α-type | α-type | α-type | α-type | α-type |
| | Moisture-confining properties (moisturizing properties) of coating film | 35 | 39 | 36 | 37 | 37 | 36 | 36 | 39 | 39 |
| | Uniform dispersibility of powder in coating film | 5.0 | 5.0 | 5.0 | 5.0 | 5.0 | 4.0 | 4.0 | 5.0 | 5.0 |
| | Brightness of coating film | 5 | 5 | 4 | 4 | 5 | 4 | 4 | 5.0 | 5.0 |
| | Less likelihood of coating film to come off against friction | 5.0 | 5.0 | 5.0 | 5.0 | 5.0 | 4.0 | 4.0 | 5.0 | 5.0 |

*1: TIPAQUE CR-50 (manufactured by Ishihara Sangyo Kaisha, Ltd.), average particle size: 250 nm, silica alumina treatment
*2: UV-Titan M160 (manufactured by Sachtleben Chemie GmbH), average particle size: 17 nm, fatty acid treatment
*3: Production Example 1, average particle size: 2.2 μm
*4: SUNSPHERE H-52 (manufactured by AGC Si-Tech, Co., Ltd.), average particle size: 5 μm
*5: OTS-2 Yellow LLXLO (manufactured by Daito Kasei Kogyo Co., Ltd.), major axis: 0.8 μm, minor axis: 0.07 μm, triethoxycaprylylsilane treatment
*6: PDM-5L (manufactured by Topy Industries Ltd.), average particle size: 7 μm
*7: Talc JA-13R (manufactured by Asada Milling Co., Ltd.), average particle size: 7 μm

TABLE 3

| | Component (mass %) | Comparative Example 1 | 2 | 3 | 4 | 5 | 6 | 7 |
|---|---|---|---|---|---|---|---|---|
| A | Stearic acid | | 2.5 | 2.5 | 2 | 2 | 0.3 | 0.5 |
| B | L-arginine | 0.2 | 0.2 | | 0.4 | 0.14 | 0.01 | 0.01 |
| C | Sodium hydroxide | 0.1 | 0.1 | 0.15 | | 0.15 | 0.015 | 0.015 |
| D | Cetostearyl alcohol | 4.5 | | 4.5 | 4.5 | 2 | 1.4 | 0.3 |
| | Behenyl alcohol | | | | | | | |
| E | Titanium oxide*1 | 0.5 | 0.5 | 0.5 | 0.5 | | 0.5 | 0.5 |
| G | Ceteareth-20 (HLB 16.1) | 0.4 | 0.4 | 0.4 | 0.4 | 0.4 | 0.4 | 0.4 |
| F | Water | Balance | Balance | Balance | Balance | Balance | Balance | Balance |
| | Total | 100 | 100 | 100 | 100 | 100 | 100 | 100 |
| | A+D | 4.5 | 2.5 | 7 | 6.5 | 4 | 1.7 | 0.8 |
| | A/(A+D) Mass ratio | 0.00 | 1.00 | 0.36 | 0.31 | 0.50 | 0.18 | 0.63 |
| | B/(B+C) Molar ratio | 31.4 | 31.4 | 0.0 | 100.0 | 17.6 | 13.3 | 13.3 |
| | (B+C)/A Molar ratio | — | 41.5 | 42.7 | 32.7 | 64.8 | 41.0 | 24.6 |
| | E/(A+D) Mass ratio | 0.11 | 0.20 | 0.071 | 0.08 | 0.00 | 0.29 | 0.63 |

TABLE 3-continued

| | | | | | | | |
|---|---|---|---|---|---|---|---|
| Absence of stickiness upon application | 3.00 | 3.00 | 3.000 | 4.00 | 5.00 | 5.00 | 5.00 |
| Presence or absence of α-type structure formation in coating film | — | — | α type | α type | α type | — | — |
| Moisture-confining properties (moisturizing properties) of coating film | 11 | 15 | 30 | 28 | 38 | 13 | 9 |
| Uniform dispersibility of powder in coating film | 1 | 2 | 2 | 2 | — | 2 | 2 |
| Brightness of coating film | 2.0 | 2.0 | 2.0 | 2.0 | 1.0 | 2.0 | 2.0 |
| Less likelihood of coating film to come off against friction | 1 | 2 | 2 | 2 | — | 1 | 1 |

| | Component (mass %) | Comparative Example | | | | | | |
|---|---|---|---|---|---|---|---|---|
| | | 8 | 9 | 10 | 11 | 12 | 13 | 14 |
| A | Stearic acid | 7 | 6 | 0.5 | 6 | 2 | 2 | 2 |
| B | L-arginine | 1 | 1 | 0.005 | 1.5 | 0.14 | 0.14 | 0.14 |
| C | Sodium hydroxide | 0.4 | 0.4 | 0.005 | 1.5 | 0.15 | 0.15 | 0.15 |
| D | Cetostearyl alcohol | 5.2 | 8 | 1.4 | 5.2 | 2 | 2 | |
| | Behenyl alcohol | | | | | | | |
| E | Titanium oxide*1 | 0.5 | 0.5 | 0.5 | 0.5 | 0.005 | 10 | 0.15 |
| G | Ceteareth-20 (HLB 16.1) | 0.4 | 0.4 | 0.4 | 0.4 | 0.4 | 0.4 | 0.5 |
| F | Water | Balance | Balance | Balance | Balance | Balance | Balance | Balance |
| Total | | 100 | 100 | 100 | 100 | 100 | 100 | 100 |
| A+D | | 12.2 | 14 | 1.9 | 11.2 | 4 | 4 | 3 |
| A/(A+D) Mass ratio | | 0.57 | 0.43 | 0.26 | 0.54 | 0.50 | 0.50 | 0.67 |
| B/(B+C) Molar ratio | | 36.4 | 36.4 | 18.6 | 18.6 | 17.6 | 17.6 | 17.6 |
| (B+C)/A Molar ratio | | 64.0 | 74.6 | 8.7 | 218.6 | 64.8 | 64.8 | 64.8 |
| E/(A+D) Mass ratio | | 0.041 | 0.036 | 0.26 | 0.04 | 0.0013 | 2.50 | 0.05 |
| Absence of stickiness upon application | | 2.000 | 1.000 | 3.00 | 2.00 | 5.00 | 5.00 | 5 |
| Presence or absence of α-type structure formation in coating film | | α type | α type | — | — | α type | α type | α type |
| Moisture-confining properties (moisturizing properties) of coating film | | 53 | 60 | 12 | 30 | 38 | 25 | 27 |
| Uniform dispersibility of powder in coating film | | 4 | 4 | 2 | 2 | 5 | 2 | 5.0 |
| Brightness of coating film | | 4.0 | 4.0 | 3.0 | 3.0 | 1.0 | 5.0 | 4.0 |
| Less likelihood of coating film to come off against friction | | 4 | 4 | 2 | 2 | 5 | 1 | 4.0 |

*1: TIPAQUE CR-50 (manufactured by Ishihara Sangyo Kaisha, Ltd.), average particle size: 250 nm, silica alumina treatment Examples 33 to 40 and Comparative Examples 15 to 17

Skin cosmetics were produced according to the composition shown in Table 4 and evaluated for the absence of stickiness upon application, the presence or absence of α-type structure formation in a coating film, the moisture-confining properties (moisturizing properties) of the coating film, and less likelihood of the coating film to come off against friction. These skin cosmetics were also evaluated for their ultraviolet protective effects. The results are also shown in Table 4.

(Production Method)

The aqueous phase components including the components (C) and (F) and L-arginine were dissolved by stirring at 70 to 80° C. to form an aqueous phase portion. Next, the oil phase components including the components (A), (D), (E), and (G), 2-amino-2-methyl-1-propanol, and octyl methoxycinnamate were dissolved by stirring at 70 to 80° C. to form an oil phase portion. The oil phase portion was added to the aqueous phase portion with stirring at 70 to 80° C., and the mixture was cooled to room temperature (30° C.) with further stirring to produce a skin cosmetic (oil-in-water emulsion cosmetic).

(Evaluation Method) Ultraviolet Protective Effect:

28.5 mg of each cosmetic was uniformly applied to each PMMA plate (Helioplate HD6, manufactured by Helioscreen; roughness: 6 μm) and dried for 15 minutes in a dark room. Then, the transmittance of a wavelength at 310 nm was measured using UV-2000S (manufactured by Labsphere Inc.). Three plates were measured per sample, and an average transmittance from 5 areas per plate, i.e., a total of 15 areas, was used in evaluation according to the following criteria:

5: Average transmittance of less than 0.5.
4: Average transmittance of 0.5 or more and less than 1.0.
3: Average transmittance of 1.0 or more and less than 1.5.
2: Average transmittance of 1.5 or more and less than 2.0.
1: Average transmittance of 2.0 or more.

TABLE 4

| | Component (mass %) | Example | | | | | |
|---|---|---|---|---|---|---|---|
| | | 33 | 34 | 35 | 36 | 37 | 38 |
| A | Stearic acid | 2.5 | 2.5 | 2.5 | 2.5 | 3.5 | 2.5 |
| B | L-arginine | 0.1 | 0.1 | 0.1 | 0.1 | 0.1 | 0.1 |
| | 2-Amino-2-methyl-1-propanol | 0.2 | 0.2 | 0.2 | 0.2 | 0.2 | 0.2 |
| C | Sodium hydroxide | 0.075 | 0.075 | 0.075 | 0.075 | 0.075 | 0.075 |
| D | Cetostearyl alcohol | 3 | 3 | 3 | 3 | 3 | 3 |

TABLE 4-continued

| | Component (mass %) | | | | | | |
|---|---|---|---|---|---|---|---|
| E | Fine titanium oxide particle*8 | 3 | | | | | |
| | Fine titanium oxide particle*9 | | 3 | | | | |
| | Fine titanium oxide particic*10 | | | 3 | | | |
| | Fine titanium oxide particle*11 | | | | 3 | | |
| | Silica*12 | | | | | 2 | |
| | Aluminum corn starch octenylsuccinate*13 | | | | | | |
| | Talc*14 | | | | | | |
| G | Ceteareth-20 (HLB 16.1) | 0.25 | 0.25 | 0.25 | 0.25 | 0.25 | 0.25 |
| | Octyl methoxycinnamate | 6 | 6 | 6 | 6 | 6 | 6 |
| F | Water | Balance | Balance | Balance | Balance | Balance | Balance |
| | Total | 100 | 100 | 100 | 100 | 100 | 100 |
| | A+D | 5.5 | 5.5 | 5.5 | 5.5 | 6.5 | 5.5 |
| | A/(A+D) Mass ratio | 0.45 | 0.45 | 0.45 | 0.45 | 0.54 | 0.45 |
| | B/(B+C) Molar ratio | 60.1 | 60.1 | 60.1 | 60.1 | 60.1 | 60.1 |
| | (B+C)/A Molar ratio | 53.4 | 53.4 | 53.4 | 53.4 | 38.2 | 53.4 |
| | E/(A+D) Mass ratio | 0.55 | 0.55 | 0.55 | 0.55 | 0.46 | 0.91 |
| | Absence of stickiness upon application | 5 | 5 | 4 | 4 | 5 | 5 |
| | Presence or absence of α type structure formation in coating film | α type | α type | α type | α type | α type | α type |
| | Moisture-confining properties (moisturizing properties) of coating film | 46 | 45 | 57 | 45 | 57 | 47 |
| | Less likelihood of coating film to come off against friction | 5 | 5 | 5 | 5 | 5 | 5 |
| | Ultraviolet protective effect | 4 | 5 | 4 | 4 | 5 | 4 |

| | | Example | | Comparative Example | | |
|---|---|---|---|---|---|---|
| | Component (mass %) | 39 | 40 | 15 | 16 | 17 |
| A | Stearic acid | 2.5 | 2.5 | 0.3 | 2.5 | 2.5 |
| B | L-arginine | 0.1 | 0.1 | 0.1 | | 0.6 |
| | 2-Amino-2-methyl-1-propanol | 0.2 | 0.2 | 0.2 | | 0.1 |
| C | Sodium hydroxide | 0.075 | 0.075 | 0.075 | 0.19 | |
| D | Cetostearyl alcohol | 3 | 3 | 3 | 3 | 3 |
| E | Fine titanium oxide particle*8 | | | | | |
| | Fine titanium oxide particle*9 | | | | | |
| | Fine titanium oxide particic*10 | | | | | |
| | Fine titanium oxide particle*11 | | | | | |
| | Silica*12 | | | | | |
| | Aluminum corn starch octenylsuccinate*13 | 2 | | | | |
| | Talc*14 | | 2 | | | |
| G | Ceteareth-20 (HLB 16.1) | 0.25 | 0.25 | 0.25 | 0.25 | 0.25 |
| | Octyl methoxycinnamate | 6 | 6 | 6 | 6 | 6 |
| F | Water | Balance | Balance | Balance | Balance | Balance |
| | Total | 100 | 100 | 100 | 100 | 100 |
| | A+D | 5.5 | 5.5 | 3.3 | 5.5 | 5.5 |
| | A/(A+D) Mass ratio | 0.45 | 0.45 | 0.09 | 0.45 | 0.45 |
| | B/(B+C) Molar ratio | 60.1 | 60.1 | 60.1 | 0.0 | 100.0 |
| | (B+C)/A Molar ratio | 53.4 | 53.4 | 445.1 | 54.1 | 52.0 |
| | E/(A+D) Mass ratio | 0.91 | 0.91 | 0.91 | 0.55 | 0.55 |
| | Absence of stickiness upon application | 5 | 5 | 2 | 2 | 3 |
| | Presence or absence of α type structure formation in coating film | α type | α type | — | α type | α type |
| | Moisture-confining properties (moisturizing properties) of coating film | 43 | 46 | 19 | 27 | 31 |
| | Less likelihood of coating film to come off against friction | 5 | 5 | 2 | 3 | 3 |
| | Ultraviolet protective effect | 5 | 4 | 1 | 1 | 2 |

*8: MT-100TV (manufactured by Tayca Corp.)), average particle size: 15 nm, (stearic acid/alumina)-treated fine titanium oxide particle
*9: TTO-V-4 (manufactured by Ishihara Sangyo Kaisha, Ltd.), average particle size: 10 nm, (stearic acid/alumina)-treated fine titanium oxide particle
*10: TEGO SUN T805 (manufactured by EVONIK Industries), average particle size: 20 nm, trimethoxycaprylylsilane-treated fine titanium oxide particle
*11: NAI-T-300 (manufactured by Miyoshi Kasei, Inc.), average particle size: 15 nm, disodium N-stearoyl-L-glutamate-treated fine titanium oxide particle
*12: Sylodent 753 (manufactured by W,R, Grace & Company), average particle size: 8 μm
*13: Dry-Flo Pure (manufactured by Akzo Nobel N.Y.), average particle size: 9 μm
*14: Talc BC (manufactured by Brenntag Specialties, Inc.), average particle size: 5 μm Examples 41 to 44

Emulsions (oil-in-water emulsion cosmetics) were produced according to the composition shown in Tables 5 to 7 and evaluated for the absence of stickiness upon application, the presence or absence of α-type structure formation in a coating film, the moisture-confining properties (moisturizing properties) of the coating film, the uniform dispersibility of the powder in the coating film, the brightness of the coating film, and less likelihood of the coating film to come off against friction. The results are also shown in Tables 5 to 7.

Production Method (1) Examples 41 and 42

The aqueous phase components including the components (B), (C), and (F), carbomer 981, and methylparaben were dissolved by stirring at 70 to 80° C. to form an aqueous phase portion. Next, the oil phase components including the components (A), (D), (E), and (G), Vaseline, and dimethicone were dissolved by stirring at 70 to 80° C. to form an oil phase portion. The oil phase portion was added to the aqueous phase portion with stirring at 70 to 80° C., and the mixture was cooled to room temperature (30° C.) with further stirring. A fragrance was added thereto with stirring to produce an emulsion (oil-in-water emulsion cosmetic).

(2) Example 43

The aqueous phase components including the components (B), (C), and (F), carbomer 981, and methylparaben were dissolved by stirring at 70 to 80° C. to form an aqueous phase portion. Next, the oil phase components including the components (A), (D), (E), and (G), ethylhexyl methoxycinnamate, and dimethicone were dissolved by stirring at 70 to 80° C. to form an oil phase portion. The oil phase portion was added to the aqueous phase portion with stirring at 70 to 80° C., and the mixture was cooled to room temperature (30° C.) with further stirring. A fragrance was added thereto with stirring to produce an emulsion (oil-in-water emulsion cosmetic).

(3) Example 44

The aqueous phase components including the components (B), (C), and (F), carbomer 981, and methylparaben were dissolved by stirring at 70 to 80° C. to form an aqueous phase portion. Next, the oil phase components including the components (A), (D), (E), and (G), benzoic acid alkyl ester, and dimethicone were dissolved by stirring at 70 to 80° C. to form an oil phase portion. The oil phase portion was added to the aqueous phase portion with stirring at 70 to 80° C., and the mixture was cooled to room temperature (30° C.) with further stirring. A fragrance was added thereto with stirring to produce an emulsion (oil-in-water emulsion cosmetic).

TABLE 5

| | Component (mass %) | Example 41 | Example 42 |
|---|---|---|---|
| A | Stearic acid | 2.5 | 2.5 |
| B | L-arginine | 0.17 | 0.17 |
| C | Sodium hydroxide | 0.2 | 0.2 |
| D | Cetostearyl alcohol | 2.3 | 2.3 |
| | Glycerin | 3 | 3 |
| E | Titanium oxide*1 | 0.5 | 1.5 |
| G | Ceteareth-20 (HLB 16.1) | 0.4 | 0.4 |
| | Laureth-3 (HLB 8) | 0.4 | 0.4 |
| | Carbomer*15 | 0.05 | 0.05 |
| | Dimethicone | 1 | 1 |
| | Methylparaben | 0.2 | 0.2 |
| | Fragrance | q.s. | q.s. |
| F | Water | Balance | Balance |
| | Total | 100 | 100 |
| | A + D | 4.8 | 4.8 |
| | A/(A + D) Mass ratio | 0.52 | 0.52 |
| | B/(B + C) Molar ratio | 16.31 | 16.31 |
| | (B + C)/A Molar ratio | 68.01 | 68.01 |
| | E/(A + D) Mass ratio | 0.104 | 0.31 |
| | Absence of stickiness upon application | 5 | 5 |
| | Presence or absence of α-type structure formation in coating film | α type | α type |
| | Moisture-confining properties (moisturizing properties) of coating film | 5 | 5 |
| | Uniform dispersibility of powder in coating film | 5 | 5 |
| | Brightness of coating film | 5 | 5 |
| | Less likelihood of coating film to come off against friction | 5 | 5 |

*1TIPAQUE CR-50 (manufactured by Ishihara Sangyo Kaisha, Ltd.), average particle size: 250 nm, silica alumina treatment
*15Carbomer 981 (manufactured by Lubrizol Advanced Materials, Inc.)

TABLE 6

| | Component (mass %) | Example 43 |
|---|---|---|
| A | Stearic acid | 2 |
| B | L-Arginine | 0.15 |
| | 2-Amino-2-methyl-1-propanol | 0.15 |
| C | Sodium hydroxide | 0.07 |
| D | Cetostearyl alcohol | 1.8 |
| | Glycerin | 3 |
| E | Titanium oxide*1 | 0.3 |
| | Fine titanium oxide particle*2 | 1.5 |
| G | Ceteareth-20 (HLB 16.1) | 0.5 |
| | Laureth-3 (HLB 8) | 0.2 |
| | Ethylhexyl methoxycinnamate | 3 |
| | Dimethicone | 1 |
| | Carbomer*15 | 0.13 |
| | Methylparaben | 0.2 |
| | Fragrance | 0.07 |
| F | Water | Balance |
| | Total | 100 |
| | A + D | 3.8 |
| | A/(A + D) Mass ratio | 0.53 |
| | B/(B + C) Molar ratio | 32.94 |
| | (B + C)/A Molar ratio | 37.14 |
| | E/(A + D) Mass ratio | 0.47 |
| | Absence of stickiness upon application | 5 |
| | Presence or absence of α-type structure formation in coating film | α type |
| | Moisture-confining properties (moisturizing properties) of coating film | 5 |
| | Uniform dispersibility of powder in coating film | 5 |
| | Brightness of coating film | 5 |
| | Less likelihood of coating film to come off against friction | 5 |

*1TIPAQUE CR-50 (manufactured by Ishihara Sangyo Kaisha, Ltd.), average particle size: 250 nm, silica alumina treatment
*2UV-Titan M160 (manufactured by Sachtleben Chemie GmbH), average particle size: 17 nm, fatty acid treatment
*15Carbomer 981 (manufactured by Lubrizol Advanced Materials, Inc.)

TABLE 7

| | Component (mass %) | Example 44 |
|---|---|---|
| A | Stearic acid | 1.7 |
| B | L-arginine | 0.1 |
| C | Sodium hydroxide | 0.11 |
| D | Cetostearyl alcohol | 1.5 |
| | Glycerin | 6 |
| E | Titanium oxide*1 | 0.3 |
| | (Lauryl methacrylate/sodium methacrylate) crosspolymer*3 | 0.3 |
| G | Ceteareth-20 (HLB 16.1) | 0.6 |
| | Benzoic acid alkyl ester (C12-15) | 1 |
| | Carbomer*15 | 0.1 |
| | Methylparaben | 0.3 |
| | Fragrance | q.s. |
| F | Water | Balance |
| | Total | 100 |
| | A + D | 3.2 |
| | A/(A + D) Mass ratio | 0.53 |

TABLE 7-continued

| Component (mass %) | Example 44 |
|---|---|
| B/(B + C) Molar ratio | 17.25 |
| (B + C)/A Molar ratio | 55.63 |
| E/(A + D) Mass ratio | 0.1875 |
| Absence of stickiness upon application | 5 |
| Presence or absence of α-type structure formation in coating film | α type |
| Moisture-confining properties (moisturizing properties) of coating film | 5 |
| Uniform dispersibility of powder in coating film | 5 |
| Brightness of coating film | 5 |
| Less likelihood of coating film to come off against friction | 5 |

*1TIPAQUE CR-50 (manufactured by Ishihara Sangyo Kaisha, Ltd.), average particle size: 250 nm, silica alumina treatment
*3Production Example 1, average particle size: 2.2 μm
*15Carbomer 981 (manufactured by Lubrizol Advanced Materials, Inc.)

Formulation Examples 1 to 3

The components (C) and (F), L-arginine, carbomer, glycerin, EDTA-2Na, and methylparaben were dissolved by stirring at 70 to 80° C. to form an aqueous phase portion. Next, the components (A), (D), (E), and (G), 2-amino-2-methyl-1-propanol, octyl methoxycinnamate, octyl salicylate, oxybenzone-3, homosalate, octocrylene, t-butylmethoxydibenzoylmethane, bis-ethylhexyloxyphenol methoxyphenyl triazine, octyl triazone, laureth-3, glyceryl stearate, benzoic acid alkyl ester, and dimethicone were dissolved by stirring at 70 to 80° C. to form an oil phase portion. The oil phase portion was added to the aqueous phase portion with stirring at 70 to 80° C., and the mixture was cooled to room temperature (30° C.) with further stirring. Then, phenoxyethanol and a fragrance were added thereto with stirring to produce an emulsion (oil-in-water emulsion cosmetic).

All of the obtained skin cosmetics offer no stickiness upon application, form a film (coating film) having a lamellar α-gel structure on the surface of the skin after being applied to the skin, produce high moisture-confining properties against water loss from the skin in a low humid environment, effectively exert the effects of the powder because the powder is uniformly dispersed in the coating film, also render the coating film less likely to come off against friction after application, and exert the sustained effects of the powder for a long time. Furthermore, these skin cosmetics are also excellent in ultraviolet protective effect.

TABLE 8

| | Component (mass %) | Formulation Example 1 | Formulation Example 2 | Formulation Example 3 |
|---|---|---|---|---|
| A | Stearic acid | 3.5 | 2.5 | 2.15 |
| B | L-arginine | 0.1 | 0.1 | |
| | 2-Amino-2-methyl-1-propanol | 0.2 | 0.2 | 0.2 |
| C | Sodium hydroxide | 0.12 | 0.075 | 0.15 |
| D | Cetostearyl alcohol | 3 | 3 | 3.15 |
| E | Fine titanium oxide particle*8 | 4 | 3 | 3 |
| | Aluminum corn starch octenylsuccinate*13 | 3 | | |
| G | Ceteareth-20 (HLB 16.1) | 0.25 | 0.25 | 0.25 |
| | Octyl methoxycinnamate | 7.5 | | 8.5 |
| | Octyl salicylate | 1 | 5 | |
| | Oxybenzone-3 | 3 | 4 | |
| | homosalate | | 5 | |
| | Octocrylene | | 2 | |
| | t-Butylmethoxydibenzoylmethane | | 3 | |
| | Bis-ethylhexyloxyphenol methoxyphenyl triazine | | | 2 |
| | Octyl triazone | | | 0.5 |
| | Benzoic acid alkyl ester (C12-15) | | | 3 |
| | Carbomer*15 | 0.1 | | 0.1 |
| | Laureth-3 | 0.3 | | 0.5 |
| | Glyceryl stearate | 0.3 | | 0.35 |
| | Dimethicone | 3 | | 5 |
| | Glycerin | | | 4.3 |
| | EDTA-2Na | | | 0.1 |
| | Phenoxyethanol | 0.4 | | 0.4 |
| | Methylparaben | 0.3 | | 0.3 |
| | Fragrance | q.s. | q.s. | q.s. |
| F | Water | Balance | Balance | Balance |
| | Total | 100 | 100 | 100 |
| | A + D | 6.5 | 5.5 | 5.3 |
| | A/(A + D) Mass ratio | 0.54 | 0.45 | 0.41 |
| | B/(B + C) Molar ratio | 48.4 | 60.1 | 37.4 |
| | (B + C)/A Molar ratio | 47.3 | 53.4 | 79.3 |
| | E/(A + D) Mass ratio | 1.08 | 0.55 | 0.57 |

*8MT-100TV (manufactured by Tayca Corp.)), average particle size: 15 nm, (stearic acid/alumina)-treated fine titanium oxide particle
*13Dry-Flo Pure (manufactured by Akzo Nobel N.V.), average particle size: 9 μm
*15Carbomer 981 (manufactured by Lubrizol Advanced Materials, Inc.)

The invention claimed is:

1. A skin cosmetic comprising the following components (A), (B), (C), (D), (E), and (F):
   (A) 0.5 to 6 mass % of a linear saturated fatty acid having 12 to 22 carbon atoms, comprising at least one selected from the group consisting of myristic acid, palmitic acid, stearic acid and behenic acid,
   (B) 0.010 to 1 mass % of an organic base comprising at least one selected from the group consisting of L-arginine, 2-amino-2-methyl-1-propanol, triethanolamine and 2-amino-2-hydroxymethyl-1,3-propanediol,
   (C) 0.015 to 0.4 mass % of an inorganic base comprising at least one selected from the group consisting of sodium hydroxide and potassium hydroxide,
   (D) 0.5 to 5.2 mass % of a linear saturated alcohol having 12 to 22 carbon atoms, comprising at least one selected from the group consisting of myristyl alcohol, cetyl alcohol, stearyl alcohol and behenyl alcohol,
   (E) 0.05 to 8.5 mass % of a powder comprising at least one selected from the group consisting of titanium oxide, a lauryl methacrylate/sodium methacrylate crosspolymer, silica, synthetic phlogopite and talc, and
   (F) water,
   wherein
   the component (D) comprises at least a linear saturated alcohol laving 12 to 20 carbon atoms, and
   the mass ratio of the component (F) to the total amount of the components (A) and (D) [(A)+(D)], (E)/[(A)+(D)], is from 0.01 to 5.

2. A skin cosmetic comprising the following components (A), (B), (C), (D), (E), and (F):
   (A) 0.5 to 6 mass % of a linear saturated fatty acid having 12 to 22 carbon atoms, comprising at least one selected from the group consisting of myristic acid, palmitic acid, stearic acid and behenic acid,
   (B) 0.010 to 1 mass % of an organic base comprising at least one selected from the group consisting of L-arginine, 2-amino-2-methyl-1-propanol, triethanolamine and 2-amino-2-hydroxymethyl-1,3-propanediol, (C) 0.015 to 0.4 mass % of an inorganic base comprising at least one selected from the group consisting of sodium hydroxide and potassium hydroxide, (D) 0.5 to 5.2 mass % of a linear saturated alcohol having 12 to 22 carbon atoms, comprising at least one selected from the group consisting of myristyl alcohol, cetyl alcohol, stearyl alcohol and behenyl alcohol, (E) 0.05 to 8.5 mass % of a powder comprising at least one selected from the group consisting of titanium oxide, a lauryl methacrylate/sodium methacrylate crosspolymer, synthetic phlogopite and talc, and (F) 50 to 98 mass % of water, wherein the component (D) comprises at least a linear saturated alcohol having 12 to 20 carbon atoms, and the mass ratio of the component (E) to the total amount of the components (A) and (D) [(A)+(D)], (E)/[(A)+(D)], is from 0.01 to 5.

3. The skin cosmetic of claim 1, further comprising (G) a nonionic surfactant, wherein the content thereof is 0.05 to 2 mass % in the whole composition.

4. The skin cosmetic of claim 3, wherein the nonionic surfactant (G) has an HLB of from 8 to 19.

5. The skin cosmetic of claim 1, wherein the component (E) comprises at least one member selected from the group consisting of titanium oxide, talc, silica, and a lauryl methacrylate/sodium methacrylate crosspolymer.

6. The skin cosmetic of claim 2, further comprising (G) a nonionic surfactant, wherein the content thereof is 0.05 to 2 mass % in the whole composition.

7. The skin cosmetic of claim 6, wherein the nonionic surfactant (G) has an HLB of from 8 to 19.

8. The skin cosmetic of claim 2, wherein the component (E) comprises at least one member selected from the group consisting of titanium oxide, talc, silica, and a lauryl methacrylate/sodium methacrylate crosspolymer.

9. The skin cosmetic of claim 1, wherein:
the linear saturated fatty acid having 12 to 22 carbon atoms (A) comprises stearic acid,
the organic base (B) comprises L-arginine,
the inorganic base (C) comprises sodium hydroxide,
the linear saturated alcohol having 12 to 22 carbon atoms (D) comprises cetostearyl alcohol, and
the powder (E) comprises titanium oxide.

10. The skin cosmetic of claim 2, wherein:
the linear saturated fatty acid having 12 to 22 carbon atoms (A) comprises stearic acid,
the organic base (B) comprises L-arginine,
the inorganic base (C) comprises sodium hydroxide,
the linear saturated alcohol having 12 to 22 carbon atoms (D) comprises cetostearyl alcohol, and
the powder (E) comprises titanium oxide.

11. The skin cosmetic of claim 1, wherein:
the linear saturated fatty acid having 12 to 22 carbon atoms (A) comprises stearic acid, and
the linear saturated alcohol having 12 to 22 carbon atoms (D) comprises cetostearyl alcohol.

12. The skin cosmetic of claim 2, wherein:
the linear saturated fatty acid having 12 to 22 carbon atoms (A) comprises stearic acid, and
the linear saturated alcohol having 12 to 22 carbon atoms (D) comprises cetostearyl alcohol.

* * * * *

UNITED STATES PATENT AND TRADEMARK OFFICE
CERTIFICATE OF CORRECTION

Page 1 of 1

PATENT NO. : 10,568,824 B2
APPLICATION NO. : 15/028809
DATED : February 25, 2020
INVENTOR(S) : Chihiro Ueyama et al.

It is certified that error appears in the above-identified patent and that said Letters Patent is hereby corrected as shown below:

In the Claims

Column 34, Lines 52-57:
"the component (D) comprises at least a linear saturated alcohol laving 12 to 20 carbon atoms, and the mass ratio of the component (F) to the total amount of the components (A) and (D) [(A)+(D)], (E)/[(A)+(D)], is from 0.01 to 5."

Should read as:
-- the component (D) comprises at least a linear saturated alcohol having 12 to 20 carbon atoms, and the mass ratio of the component (E) to the total amount of the components (A) and (D) [(A)+(D)], (E)/[(A)+(D)], is from 0.01 to 5. --

Signed and Sealed this
Twelfth Day of May, 2020

Andrei Iancu
*Director of the United States Patent and Trademark Office*